United States Patent
Hall et al.

(10) Patent No.: US 10,280,447 B2
(45) Date of Patent: May 7, 2019

(54) SUBSTITUTED IMIDAZO[1,2-A]PYRAZINES TETHERED TO ENERGY ACCEPTORS

(71) Applicant: PROMEGA CORPORATION, Madison, WI (US)

(72) Inventors: Mary Hall, Waunakee, WI (US); Thomas Kirkland, Atascadero, CA (US); Thomas Machleidt, Madison, WI (US); Anton Shakhmin, Santa Clara, CA (US); Joel R. Walker, San Luis Obispo, CA (US); Keith V. Wood, Mount Horeb, WI (US); Wenhui Zhou, San Luis Obispo, CA (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 15/800,649

(22) Filed: Nov. 1, 2017

(65) Prior Publication Data
US 2018/0119200 A1    May 3, 2018

Related U.S. Application Data

(60) Provisional application No. 62/415,671, filed on Nov. 1, 2016.

(51) Int. Cl.
| | |
|---|---|
| C07D 487/04 | (2006.01) |
| C12Q 1/66 | (2006.01) |
| A61K 49/00 | (2006.01) |
| C07D 519/00 | (2006.01) |
| C07D 491/22 | (2006.01) |
| C07D 498/14 | (2006.01) |
| G01N 21/76 | (2006.01) |

(52) U.S. Cl.
CPC ............ *C12Q 1/66* (2013.01); *A61K 49/0052* (2013.01); *C07D 487/04* (2013.01); *C07D 491/22* (2013.01); *C07D 498/14* (2013.01); *C07D 519/00* (2013.01); *G01N 21/763* (2013.01)

(58) Field of Classification Search
CPC .................................................. C07D 487/04
USPC ........................................................ 544/350
See application file for complete search history.

(56) References Cited

U.S. PATENT DOCUMENTS

| | | |
|---|---|---|
| 8,557,970 B2 | 10/2013 | Encell et al. |
| 8,669,103 B2 | 3/2014 | Binkowski et al. |
| 2008/0248511 A1 | 10/2008 | Daily et al. |
| 2011/0275134 A1 | 11/2011 | Bouvier et al. |
| 2012/0107849 A1 | 5/2012 | Klaubert et al. |
| 2012/0117667 A1 | 5/2012 | Klaubert et al. |
| 2013/0130289 A1 | 5/2013 | Benink et al. |

FOREIGN PATENT DOCUMENTS

| | | |
|---|---|---|
| WO | WO 2003/040100 | 5/2003 |
| WO | WO 2012/061530 | 5/2012 |
| WO | WO 2013/078244 | 5/2013 |

OTHER PUBLICATIONS

Adamczyk, et al. Tetrahedron, 59(41), 2003, 8129-8142.*
U.S. Pat. No. 9,790,537, U.S. Appl. No. 14/609,372, Zhou et al., filed Oct. 17, 2017.
U.S. Pat. No. 9,924,073, U.S. Appl. No. 15/431,961, Shakhmin et al., filed Mar. 20, 2018.
U.S. Pat. No. 9,927,430, U.S. Appl. No. 14/608,910, Zhou et al., filed Mar. 27, 2018.
U.S. Appl. No. 15/887,735, Shakhmni et al., filed Feb. 2, 2018.
U.S. Appl. No. 62/295,363, Shakhmin et al., filed Feb. 15, 2016.
2016/0376568, U.S. Appl. No. 15/192,420, Duellman et al., filed Dec. 29, 2016.
Carruthers, Some Modern Methods of Organic Synthesis, 3rd Edition, Cambridge University Press, Cambridge, 1987.
Cross et al., "IUPAC Commission on Nomeclature of Organic Chemistry. Rules for the Nomeclature of Organic Chemistry. Section E: Stereochemistry (Recommendations 1974)," Pure & Appl. Chem., 1976, vol. 45 pp. 13-30.
Furniss, Hannaford, Smith, and Tatchell, "Vogel's Textbook of Practical Organic Chemistry," 5th edition (1989).
Hall et al., "Engineered Luciferase Reporter from a Deep Sea Shrimp Utilizing a Novel Imidazopyrazinone Substrate," ACS Chemical Biology, 2012, vol. 7, No. 11, pp. 1848-1857.
Hirayama et al., "Fluorogenic probes reveal a role of GLUT4 N-glycosylation in intracellular trafficking," Nature Chemical Biology, 2016, vol. 12, pp. 853-859.

(Continued)

*Primary Examiner* — Douglas M Willis
(74) *Attorney, Agent, or Firm* — Anne M. Reynolds; Casimir Jones, S.C.

(57) ABSTRACT

Described are substituted imidazo[1,2-a]pyrazine compounds of formula (I), which are coelenterazine analogs, methods for making the compounds, kits comprising the compounds, and methods of using the compounds for the detection of luminescence in luciferase-based assays.

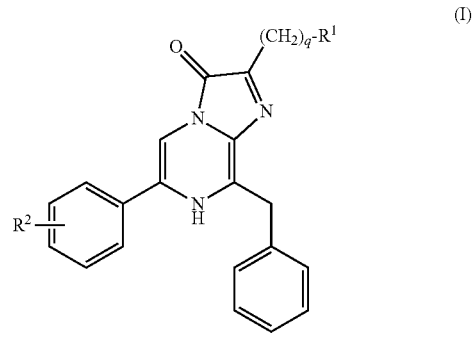

(I)

20 Claims, 7 Drawing Sheets
Specification includes a Sequence Listing.

(56) References Cited

OTHER PUBLICATIONS

Invitrogen by Thermo Fisher Scientific, The Molecular Probes Handbook, A Guide to Fluorescent Probes and Labeling Technologies, 11th edition, 2010.
Kojima et al., "Rational Design and Development of Near-Infrared-Emitting Firefly Luciferins Available In Vivo," Angewandte Chemie International Edition, 2013, 52: 1175-1179.
Larock, Comprehensive Organic Transformations, VCH Publishers, Inc., New York, 1989.
Lavis et al., "Bright Building Blocks for Chemical Biology," ACS Chemical Biology, 2014, 9, 855-866.
Lindberg et al., "Development of cell-impermeable coelenterazine derivatives," Chemical Science, 2013, 4(12): 4395-4400.
Periodic Table of the Elements, CAS version, Handbook of Chemistry and Physics, 75th Ed., 1994.
Smith and March, March's Advanced Organic Chemistry, 5th Edition, John Wiley & Sons, Inc., New York, 2001.
Sorrell, Organic Chemistry, University Science Books, Sausalito, 1999.
Wuts and Greene, Greene's Protective Groups in Organic Synthesis (4th ed.), John Wiley & Sons, NY (2006).
International Search Report and Written Opinion for Application No. PCT/US2017/059495 dated Feb. 12, 2018 (14 pages).
Invitation to Pay Additional Fees for Application No. PCT/US2017/064229 dated Mar. 13, 2018 (13 pages).
International Search Report and Written Opinion for Application No. PCT/US2017/064229 dated May 16, 2018 (18 pages).

* cited by examiner

SUBSTITUTED IMIDAZO[1,2-A]PYRAZINES TETHERED TO ENERGY ACCEPTORS

CROSS-REFERENCE TO RELATED APPLICATIONS

This application claims priority to U.S. Provisional Patent Application No. 62/415,671, filed on Nov. 1, 2016, the entire contents of which are incorporated herein by reference.

TECHNICAL FIELD

The present disclosure relates to coelenterazine analogues, methods for making coelenterazine analogues, and methods of using coelenterazine analogues in luciferase-based assays.

BACKGROUND

Bioluminescent assays are used extensively in the investigation of cellular physiology, especially processes associated with gene expression. In particular, luciferase reporter enzymes are quite valuable tools in this field, and, to date, there has been intense protein engineering to obtain small and environmentally insensitive luciferases that may be useful in bioluminescent assays. There exist a number of efficient luciferase reporters enabling whole-cell biosensor measurements, drug discovery through high-throughput screening, and in vivo imaging, which also permits the study of protein-protein interactions in living cells, apoptosis, and cell viability. Luciferases that use coelenterazine and coelenterazine analogues as substrates are among the most widely used systems due to their brightness and acceptance in whole cell applications.

However, these reactions are inherently limited by the inherent emission wavelength of the system.

SUMMARY

Many known coelenterazine analogues have deficiencies, which limit their effectiveness as luciferase substrates and usefulness in luciferase-based luminescence assays. For bioluminescent resonance energy transfer (BRET) assays, the performance of the luciferase reaction may be limited by the emission wavelength of the substrate in the assay system. The activity of a substrate may also be affected by the tolerance of the enzyme's active site for the substrate's structure and properties. Accordingly, there exists a need for coelenterazine analogues with improved properties.

The disclosed compounds may include a coelenterazine analog core, a covalent chain linker, and an energy acceptor. The coelenterazine analog core may bind to a luciferase at the enzyme's binding site. The covalent chain may extend out of the enzyme's binding pocket such that the energy acceptor is located in proximity of the enzyme-bound coelenterazine analog core. The disclosed compounds thus are structurally distinctive from the conventional luciferase substrates in that the luciferase substrate core is covalently tethered to an energy acceptor. Yet, the disclosed compounds unexpectedly maintain the luciferase substrate activities that emit bioluminescence, while simultaneously allowing for BRET to occur due to the proximity between the covalently linked coelenterazine analog core and the energy acceptor.

In one aspect, disclosed are compounds of formula (I),

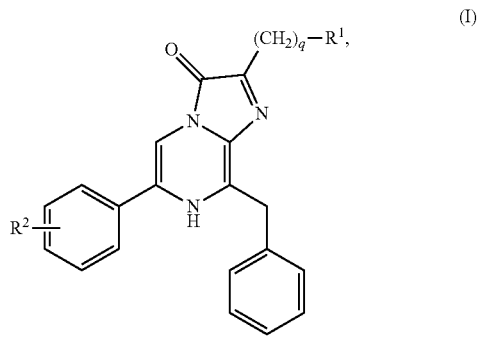

or a tautomer, or a pharmaceutically acceptable salt thereof, wherein $R^1$ is

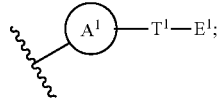

$R^2$ is absent or a substituent selected from the group consisting of alkyl, haloalkyl, halogen, —OH, and —NH$_2$;

$A^1$ is aryl, heteroaryl, heterocycle, or cycloalkyl;

$T^1$ is alkyl, alkenyl, alkynyl, or heteroalkyl;

$E^1$ is an energy acceptor; and q is 0, 1, or 2;

wherein said alkyl, alkenyl, alkynyl, heteroalkyl, aryl, heteroaryl, heterocycle, and cycloalkyl, at each occurrence, are independently substituted or unsubstituted.

Also disclosed are methods of making the compounds, kits comprising the compounds, and methods of using the compounds as luciferase substrates in luciferase-based luminescence assays.

BRIEF DESCRIPTION OF THE DRAWINGS

FIG. 2A shows the spectral profile of 10 uM TAK-0043 with 1 uM NanoLuc® and 1 uM NanoLuc-HaloTag fusion enzyme. FIG. 2B shows the peak for coelenterazine emission at 460 nm is nearly invisible. FIG. 2C shows the spectral profile of 1 uM TAK-0043 with 1 uM NanoLuc® and 1 uM NanoLuc-HaloTag fusion enzyme. FIG. 2D shows the spectral profile of 1 uM TAK-0043 with 3.3 uM NanoLuc® and 3.3 uM NanoLuc-HaloTag fusion enzyme.

DETAILED DESCRIPTION

Figure 1:
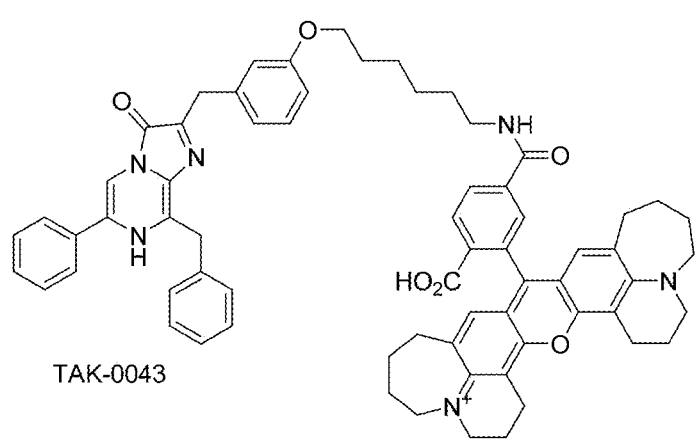
FIG. 1 shows a sample coelenterazine analogue, TAK-0043. In blue is the coelenterazine, in red is a sample acceptor (in this case the NCT dye), and in green is the linker which allows the coelenterazine to enter the NanoLuc® pocket and the NCT dye to remain outside the pocket while still being covalently attached.

Disclosed herein are compounds comprising coelenterazines analogues. The disclosed compounds may include a coelenterazine analog core, a covalent chain linker, and an energy acceptor. The coelenterazine analog core may bind to a luciferase at the enzyme's binding site. The covalent chain may extend out of the enzyme's binding pocket such that the energy acceptor is located in proximity of the enzyme-bound coelenterazine analog core. The energy acceptor may be capable of undergoing efficient BRET. The disclosed compounds thus are structurally distinctive from the conventional luciferase substrates in that the luciferase substrate core is covalently tethered to an energy acceptor. The disclosed compounds unexpectedly maintain the luciferase substrate activities that emit bioluminescence while simultaneously allowing for BRET to occur due to the proximity between the covalently linked coelenterazine analog core and the energy acceptor.

The disclosed compounds may be useful substrates of proteins that utilize coelenterazine to produce luminescence including, but not limited to, luciferases and photoproteins found in various marine organisms such as cnidarians (e.g., *Renilla* luciferase), jellyfish (e.g., aequorin from the *Aequorea* jellyfish) and decapods luciferases (e.g., luciferase complex of *Oplophorus gracilirostris*). The disclosed coelenterazine analogues may be tethered to a variety of energy acceptors by a stable linker. The acceptor can efficiently accept energy from the excited coelenterazine and emit at a longer wavelength, thus shifting the wavelength of emission produced by the coelenterazine/luciferase reaction. In comparison to coelenterazine, tethered coelenterazine analogues generate emission wavelengths that are shifted to the emission wavelength of the attached energy acceptor group. The tethered coelenterazines may be tethered to a variety of energy acceptors in order to modulate the wavelength of light emitted from the system.

Also disclosed herein are methods of making the disclosed compounds. The described methodology enables access to coelenterazines tethered to a variety of energy acceptors and can be performed under mild conditions utilizing a wide variety of readily available starting materials. The disclosed synthetic methodology unexpectedly provides a variety of new applications and advancements in bioluminescence technology based on coelenterazine analogues.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl" as used herein, means a straight or branched, saturated hydrocarbon chain containing from 1 to 10 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl" as used herein, means a hydrocarbon chain containing from 2 to 10 carbon atoms with at least one carbon-carbon double bond. The alkenyl group may be substituted or unsubstituted. For example, the alkenyl group may be substituted with an aryl group, such as a phenyl.

The term "alkynyl" as used herein, means a hydrocarbon chain containing from 2 to 10 carbon atoms with at least one carbon-carbon triple bond. The alkynyl group may be substituted or unsubstituted. For example, the alkynyl group may be substituted with an aryl group, such as a phenyl.

The term "alkoxyalkyl" as used herein, refers to an alkoxy group, as defined herein, appended to the parent molecular moiety through an alkyl group, as defined herein.

The term "alkylene", as used herein, refers to a divalent group derived from a straight or branched chain hydrocarbon of 1 to 10 carbon atoms, for example, of 2 to 5 carbon atoms. Representative examples of alkylene include, but are not limited to, —$CH_2CH_2$—, —$CH_2CH_2CH_2$—, —$CH_2CH_2CH_2CH_2$—, and —$CH_2CH_2CH_2CH_2CH_2$—.

The term "aryl" as used herein, refers to a phenyl group, or bicyclic aryl or tricyclic aryl fused ring systems. Bicyclic fused ring systems are exemplified by a phenyl group appended to the parent molecular moiety and fused to a phenyl group. Tricyclic fused ring systems are exemplified by a phenyl group appended to the parent molecular moiety and fused to two other phenyl groups. Representative examples of bicyclic aryls include, but are not limited to, naphthyl. Representative examples of tricyclic aryls include, but are not limited to, anthracenyl. The monocyclic, bicyclic, and tricyclic aryls are connected to the parent molecular moiety through any carbon atom contained within the rings, and can be unsubstituted or substituted.

The term "cycloalkyl" as used herein, refers to a carbocyclic ring system containing three to ten carbon atoms and zero heteroatoms, and optionally containing 1 or 2 double bonds. Representative examples of cycloalkyl include, but are not limited to, cyclopropyl, cyclobutyl, cyclopentyl, cyclohexyl, cycloheptyl, cyclooctyl, cyclononyl and cyclodecyl.

The term "cycloalkenyl" as used herein, means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl.

The term "fluoroalkyl" as used herein, means an alkyl group, as defined herein, in which one, two, three, four, five, six, seven or eight hydrogen atoms are replaced by fluorine. Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "alkoxyfluoroalkyl" as used herein, refers to an alkoxy group, as defined herein, appended to the parent molecular moiety through a fluoroalkyl group, as defined herein.

The term "fluoroalkoxy" as used herein, means at least one fluoroalkyl group, as defined herein, is appended to the parent molecular moiety through an oxygen atom. Representative examples of fluoroalkyloxy include, but are not limited to, difluoromethoxy, trifluoromethoxy and 2,2,2-trifluoroethoxy.

The term "halogen" or "halo" as used herein, means Cl, Br, I, or F.

The term "haloalkyl" as used herein, means an alkyl group, as defined herein, in which one, two, three, four, five, six, seven or eight hydrogen atoms are replaced by a halogen.

The term "haloalkoxy" as used herein, means at least one haloalkyl group, as defined herein, is appended to the parent molecular moiety through an oxygen atom.

The term "heteroalkyl" as used herein, means an alkyl group, as defined herein, in which one or more of the carbon atoms has been replaced by a heteroatom selected from S, Si, O, P and N. The heteroatom may be oxidized. Representative examples of heteroalkyls include, but are not limited to, alkyl ethers, secondary and tertiary alkyl amines, amides, and alkyl sulfides.

The term "heteroaryl" as used herein, refers to an aromatic monocyclic ring or an aromatic bicyclic ring system or an aromatic tricyclic ring system. The aromatic monocyclic rings are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. The tricyclic heteroaryl groups are exemplified by a monocyclic heteroaryl ring appended to the parent molecular moiety and fused to two of a monocyclic cycloalkyl group, as defined herein, a monocyclic aryl group, as defined herein, a monocyclic heteroaryl group, as defined herein, or a monocyclic heterocycle, as defined herein. Representative examples of monocyclic heteroaryl include, but are not limited to, pyridinyl (including pyridin-2-yl, pyridin-3-yl, pyridin-4-yl), pyrimidinyl, pyrazinyl, thienyl, furyl, thiazolyl, thiadiazolyl, isoxazolyl, pyrazolyl, and 2-oxo-1,2-dihydropyridinyl. Representative examples of bicyclic heteroaryl include, but are not limited to, chromenyl, benzothienyl, benzodioxolyl, benzotriazolyl, quinolinyl, thienopyrrolyl, thienothienyl, imidazothiazolyl, benzothiazolyl, benzofuranyl, indolyl, quinolinyl, imidazopyridine, benzooxadiazolyl, and benzopyrazolyl. Representative examples of tricyclic heteroaryl include, but are not limited to, dibenzofuranyl and dibenzothienyl. The monocyclic, bicyclic, and tricyclic heteroaryls are connected to the parent molecular moiety through any carbon atom or any nitrogen atom contained within the rings, and can be unsubstituted or substituted.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, 1,3-dimethylpyrimidine-2,4(1H,3H)-dione, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "hydroxyl" as used herein, means an —OH group.

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_3$-alkyl" refers to an alkyl substituent containing from 1 to 3 carbon atoms.

The term "substituents" refers to a group "substituted" on an aryl, heteroaryl, phenyl or pyridinyl group at any atom of that group. Any atom can be substituted.

The term "substituted" refers to a group that may be further substituted with one or more non-hydrogen substituent groups. Substituent groups include, but are not limited to, halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

The term "bioluminescence" or "luminescence" may refer to light produced as a result of a reaction between an enzyme and a substrate that generates light. Examples of such enzymes (bioluminescent enzymes) include *Oplophorus* luciferase, e.g., *Oplophorus gracilirostris*, firefly luciferase, e.g. *Photinus pyralis* or *Photuris pennsylvanica*, click beetle luciferase, *Renilla* luciferase, cypridina luciferase, Aequorin photoprotein, obelin photoprotein and the like.

The term "coelenterazine substrate" refers to a class of reporter molecules that luminesce when acted upon by a wide variety of bioluminescent proteins such as luciferases (e.g., marine luciferases). Coelenterazine substrates include coelenterazine as well as analogs and derivatives thereof.

The term "energy acceptor" or "acceptor molecule" refers to any small molecule (e.g., chromophore), macromolecule (e.g., autofluorescent protein, phycobiliproteins, nanoparticle, surface, etc.), or molecular complex that produces a readily detectable signal in response to energy absorption (e.g., resonance energy transfer). In certain embodiments, an energy acceptor is a fluorophore or other detectable chromophore. Suitable fluorophores include, but are not limited to: xanthene derivatives (e.g., fluorescein, rhodamine, Oregon green, eosin, Texas red, etc.), cyanine derivatives (e.g., cyanine, indocarbocyanine, oxacarbocyanine, thiacarbocyanine, merocyanine, etc.), naphthalene derivatives (e.g., dansyl and prodan derivatives), oxadiazole derivatives (e.g., pyridyloxazole, nitrobenzoxadiazole, benzoxadiazole, etc.), pyrene derivatives (e.g., cascade blue), oxazine derivatives (e.g., Nile red, Nile blue, cresyl violet, oxazine 170, etc.), acridine derivatives (e.g., proflavin, acridine orange, acridine yellow, etc.), arylmethine derivatives (e.g., auramine, crystal violet, malachite green, etc.), tetrapyrrole derivatives (e.g., porphin, phtalocyanine, bilirubin, etc.), CF dye (Biotium), BODIPY (Invitrogen), ALEXA FLuoR (Invitrogen), DYLIGHT FLUOR (Thermo Scientific, Pierce), ATTO and TRACY (Sigma Aldrich), FluoProbes (Interchim), DY and MEGASTOKES (Dyomics), SULFO CY dyes (CYANDYE, LLC), SETAU AND SQUARE DYES (SETA BioMedicals), QUASAR and CAL FLUOR dyes (Biosearch Technologies), SURELIGHT DYES (APC, RPE, PerCP, Phycobilisomes)(Columbia Biosciences), APC, APCXL, RPE, BPE (Phyco-Biotech), autofluorescent proteins (e.g., YFP, RFP, mCherry, mKate), quantum dot nanocrystals, etc. Suitable fluorophores include, for example, those described in Lavis et al., *Bright Building Blocks for Chemical Biology*, ACS Chem. Biol., 2014, 9, 855-866. Suitable fluorophores also include, for example, those described in *The Molecular Probes Handbook—A Guide to Fluorescent Probes and Labeling Technologies,* 11th Edition (2010), ThermoFisher Scientific. In some embodiments, a fluorophore is a rhodamine analog (e.g., carboxy rhodamine analog). In certain embodiments, energy acceptors include but are not limited to small molecule fluorescent dyes such as NCT, quenchers, fluorescent particles such as Quantum dots, luminescent metal complexes, and any other known energy acceptors.

As used herein, the term "halogen" or "halo" refers to a fluoro, chloro, bromo or iodo radical.

The term "luminescent enzyme," "bioluminescent enzyme," or "luciferase" as used interchangeably herein refers to a class of oxidative enzymes used in bioluminescence wherein the enzyme produces and emits light when given a substrate. The luciferase may be a naturally occurring, recombinant, or mutant luciferase that uses a luciferase substrate. The luciferase substrate may be luciferin, a luciferin derivative or analog, a preluciferin derivative or analog, a coelenterazine, or a coelenterazine derivative or analog. The luminescent enzyme, if naturally occurring, may be obtained easily by the skilled person from an organism. If the luminescent enzyme is one that occurs naturally or is a recombinant or mutant luminescent enzyme, e.g. one which retains activity in a luciferase-coelenterazine or luciferase-luciferin reaction of a naturally occurring luminescent enzyme, it can be obtained readily from a culture of bacteria, yeast, mammalian cells, insect cells, plant cells, or the like, transformed to express a nucleic acid encoding the luminescent enzyme. Further, the recombinant or mutant luminescent enzyme can be derived from an in vitro cell-free system using a nucleic acid encoding the luciferase. Suitable luminescent enzymes include luciferases derived from bioluminescent decapods, such as from the Oplophoroidea (e.g. *Oplophorus*-derived luciferases), beetle luciferases (e.g., *Photinus pyralis, Photuris pennsylvanica*, etc.), marine organisms such as cnidarians (e.g., *Renilla* luciferase), Aristeidae, Solenoceridae, Luciferidae, Sergestidae, Pasipheidae and Thalassocarididae decapoda families, copepod luciferases, such as *Gaussia* luciferase, such as *Gaussia princeps* luciferase, *Metridia* luciferases, such as *Metridia longa* and *Metridia pacifica* luciferases, *Vargula* luciferases, such as *Vargula hilgendorfii* luciferase, *Pleuromamma xiphias* luciferase, and photoproteins, such as Aequorin, and variants, recombinants, and mutants thereof.

A "luminescent reaction mixture" contains materials that will allow the luminescent enzyme to generate a light signal, i.e., luminescence. The mixture may also contain the enzyme, e.g., the luciferase enzyme or luciferase. The materials, and the particular concentrations and/or amounts, needed to generate a luminescent signal will vary depending on the luminescent enzyme used as well as the type of assay being performed. Often other materials will be added to the solution including: a buffer to maintain the reaction at the proper pH, an additive such as PRIONEX or Bovine serum albumin (BSA) to help maintain enzyme activity, reducing agents, detergents, etc.

As used herein, the terms "*Oplophorus* luciferase" and "*Oplophorus*-derived luciferase" are used interchangeably and refer to a luciferase secreted from the deep-sea shrimp *Oplophorus gracilirostris* (e.g., SEQ ID NO: 1), including wild-type, variants, and mutants thereof. For example, suitable *Oplophorus* luciferase variants are described in U.S. Pat. Nos. 8,557,970 and 8,669,103, each of which is incorporated herein by reference in its entirety. Exemplary *Oplophorus*-derived luciferases include, for example, that of SEQ ID NO: 2 (also interchangeably referred to herein as "NanoLuc", "Nluc," "Nluc luciferase," and "Nluc enzyme").

As used herein, the term "reporter moiety" may refer to a moiety that, under appropriate conditions, directly or indirectly generates a detectable signal. Exemplary reporter moieties include, but are not limited to, fluorophores, luminescent molecules, dyes, radiolabels and substrates for enzymes such as luciferase. In some embodiments, a reporter moiety may indirectly generate a detectable signal, for example, when the reporter moiety is a substrate for an enzyme. The reaction of the enzyme with the substrate then produces a detectable signal such as fluorescence or luminescence. As used herein, the term "bioluminescent reporter moiety" may refer to a moiety that is a substrate for a luciferase. For example, the bioluminescent reporter moiety can be a luciferin, a luciferin derivative, e.g., pre-luciferin, aminoluciferin, quionolyl-luciferin, naphthyl luciferin, fluoroluciferin, chloroluciferin, precursors of luciferin derivatives, a coelenterazine or a coelenterazine derivative or analog, e.g., furimazine. The luminescent signal generated may be detected using a luminometer. As used herein, the term "fluorescent reporter moiety" may refer to a moiety that fluoresces. For example, the fluorescent reporter moiety may be a fluorophore, such as coumarin, rhodamine 110 (R110), fluorescein, DDAO (7-hydroxy-9H-(1,3-dichloro-9,9-dimethylacridin-2-one)), resorufin, cresyl violet, sily xanthene, or carbopyronine. Fluorescence may be detected using a fluorometer.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. COMPOUNDS

In one aspect, disclosed are compounds of formula (I):

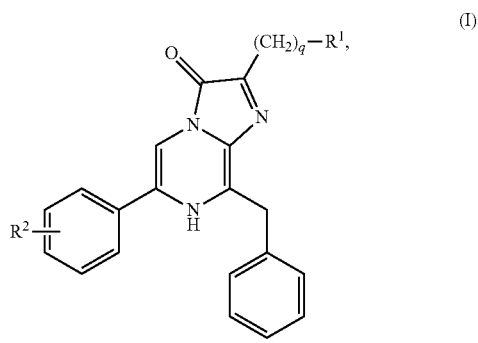

or a tautomer, or a pharmaceutically acceptable salt thereof, wherein $R^1$ is

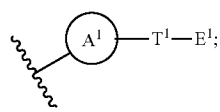

$R^2$ is absent or a substituent selected from the group consisting of alkyl, haloalkyl, halogen, —OH, and —NH$_2$;

$A^1$ is aryl, heteroaryl, heterocycle, or cycloalkyl;

$T^1$ is alkyl, alkenyl, alkynyl, or heteroalkyl;

$E^1$ is an energy acceptor; and q is 0, 1, or 2;

wherein said alkyl, alkenyl, alkynyl, heteroalkyl, aryl, heteroaryl, heterocycle, and cycloalkyl, at each occurrence, are independently substituted or unsubstituted.

In certain embodiments, $A^1$ is aryl, heteroaryl, heterocycle, or cycloalkyl, wherein said aryl, heteroaryl, heterocycle, and cycloalkyl are independently substituted with 0, 1, 2, 3, 4, 5, 6, 7, 8, 9, or 10 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl.

In certain embodiments, $A^1$ is optionally substituted phenyl. In certain embodiments, $A^1$ is phenyl optionally substituted with 0, 1, 2, 3, or 4 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl. In certain embodiments, $A^1$ is phenyl optionally substituted with 0, 1, 2, 3, or 4 substituents, wherein each substituent is independently halogen.

In certain embodiments, $A^1$ is optionally substituted furyl. In certain embodiments, $A^1$ is furyl optionally substituted with 0, 1, 2, 3, or 4 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl.

In certain embodiments, $T^1$ is alkyl, alkenyl, alkynyl, or heteroalkyl (i.e., where one or more carbon atoms are replaced with a heteroatom or heteroatom group), wherein said alkyl, alkenyl, alkynyl, and heteroalkyl are independently substituted with 0, 1, 2, 3, 4, 5, 6, 7, 8, 9, or 10 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl.

In certain embodiments, $T^1$ is $C_1$-$C_{30}$-alkyl, $C_2$-$C_{30}$-alkenyl, $C_2$-$C_{30}$-alkynyl, or $C_1$-$C_{30}$-heteroalkyl (i.e., where one or more carbon atoms are replaced with a heteroatom or heteroatom group), wherein said $C_1$-$C_{30}$-alkyl, $C_2$-$C_{30}$-alkenyl, $C_2$-$C_{30}$-alkynyl, and $C_1$-$C_{30}$-heteroalkyl are independently substituted with 0, 1, 2, 3, 4, 5, 6, 7, 8, 9, or 10 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl.

In certain embodiments, $T^1$ is optionally substituted heteroalkyl.

In certain embodiments, $T^1$ is —(O—CR$^{1a}$R$^{1b}$—CR$^{1a}$R$^{1b}$)$_m$-Q- or —O—(CR$^{1a}$R$^{1b}$)$_n$-Q-, wherein m is 1-30;

n is 1-30;

Q at each occurrence is independently —NH—CO—, —CO—NH—, —CO—O—, —O—CO—, or —O—CO—NH—; and $R^{1a}$ and $R^{1b}$ at each occurrence is independently hydrogen or $C_1$-$C_4$ alkyl.

In certain embodiments, $T^1$ is a group of the formula:

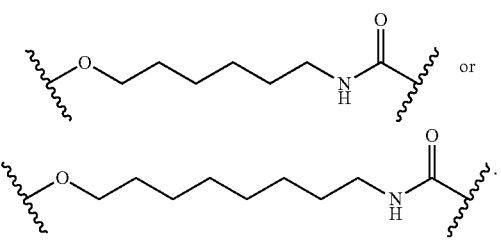

In certain embodiments, $T^1$ is a group of the formula:

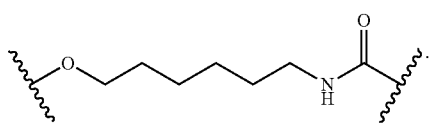 [SMILES: *OCCCCCCNC(*)=O]

In certain embodiments, $R^2$ is absent. In certain embodiments, $R^2$ is —OH or —NH$_2$.

In certain embodiments, the energy acceptor $E^1$ is a fluorescent dye, a quencher, a fluorescent particle (e.g., quantum dots), a luminescent metal complex, a combination of any of the foregoing, or an analogue of any of the foregoing. In certain embodiments, the energy acceptor $E^1$ is a fluorescent dye, such as Non-ChloroTOM (NCT), an Atto dye (such as Atto 665, Atto 610, and Atto 680), fluorescein, or a rhodamine dye (such as Oregon Green or tetramethylrhodamine). In certain embodiments, the energy acceptor $E^1$ is a fluorescent Non-ChloroTOM (NCT) dye. Suitable energy acceptors also include, for example, rhodamines, silyl rhodamines, and cyanines.

In certain embodiments, the energy acceptor has the formula:

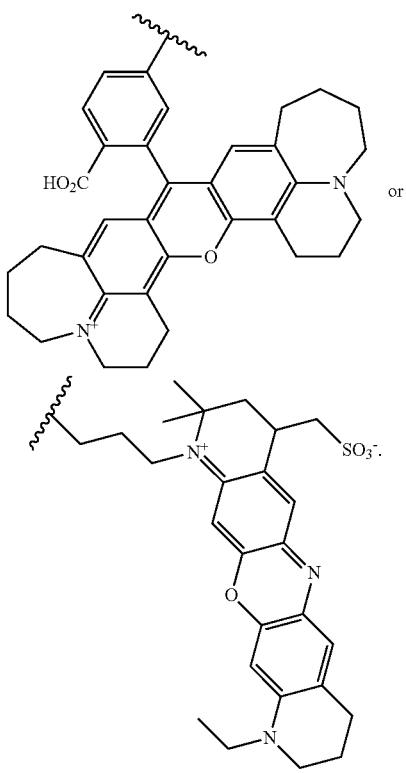

or

In certain embodiments, the energy acceptor has the formula:

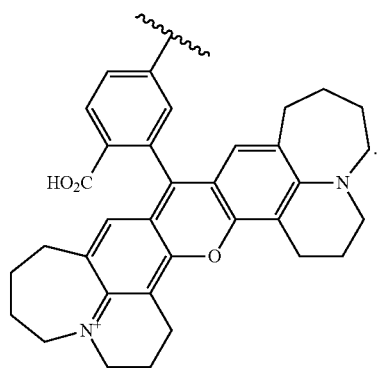 [SMILES: *c1ccc(C(=O)O)c(C2=c3cc4c5c(c3Oc3c2cc2c6c3CCCN6CCCC2)CCC[N+]=5CCCC4)c1]

In certain embodiments, q is 0. In certain embodiments, q is 1. In certain embodiments, q is 2.

In certain embodiments, the compound of formula (I) has formula (I-a):

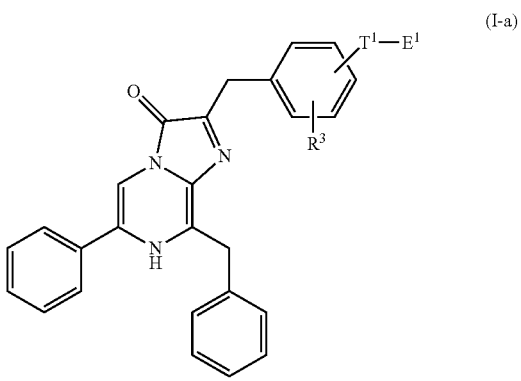

(I-a)

wherein $R^3$ is absent or halogen.

In certain embodiments, the compound of formula (I) has formula (I-a1), (I-a2), or (I-a3), wherein $E^1$ is a dye, such as a fluorescent dye.

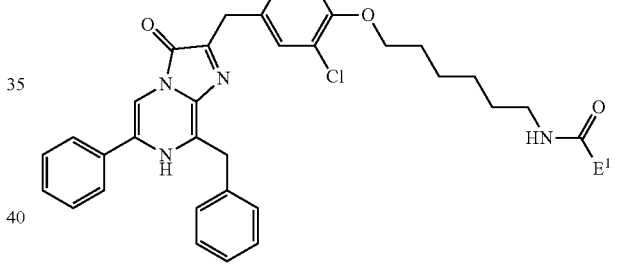

(I-a1)

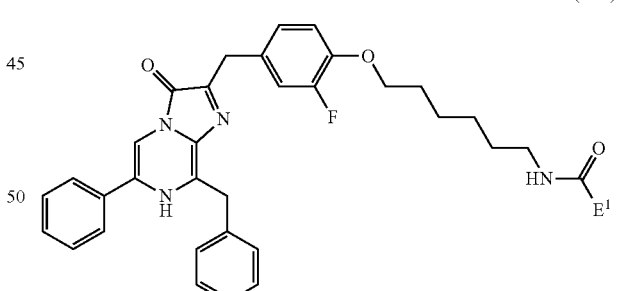

(I-a2)

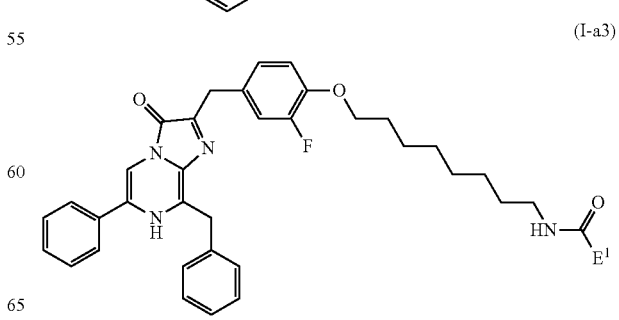

(I-a3)

In certain embodiments, the compound of formula (I) has formula (I-a1), (I-a2), or (I-a3), wherein $E^1$ is a fluorescent dye, such as NCT or Atto 655.

In certain embodiments, the compound of formula (I) has formula (I-a1) or (I-a2), wherein $E^1$ is a dye, such as fluorescent NCT dye.

wherein n is an integer selected from 1-30. In certain embodiments, n is an integer selected from 6-12, such as 6, 8, 10, or 12. In certain embodiments, n is 6 or 8. In certain embodiments, n is 6. In certain embodiments, n is 8.

In certain embodiments, the compound of formula (I) has formula (I-c) or (I-d):

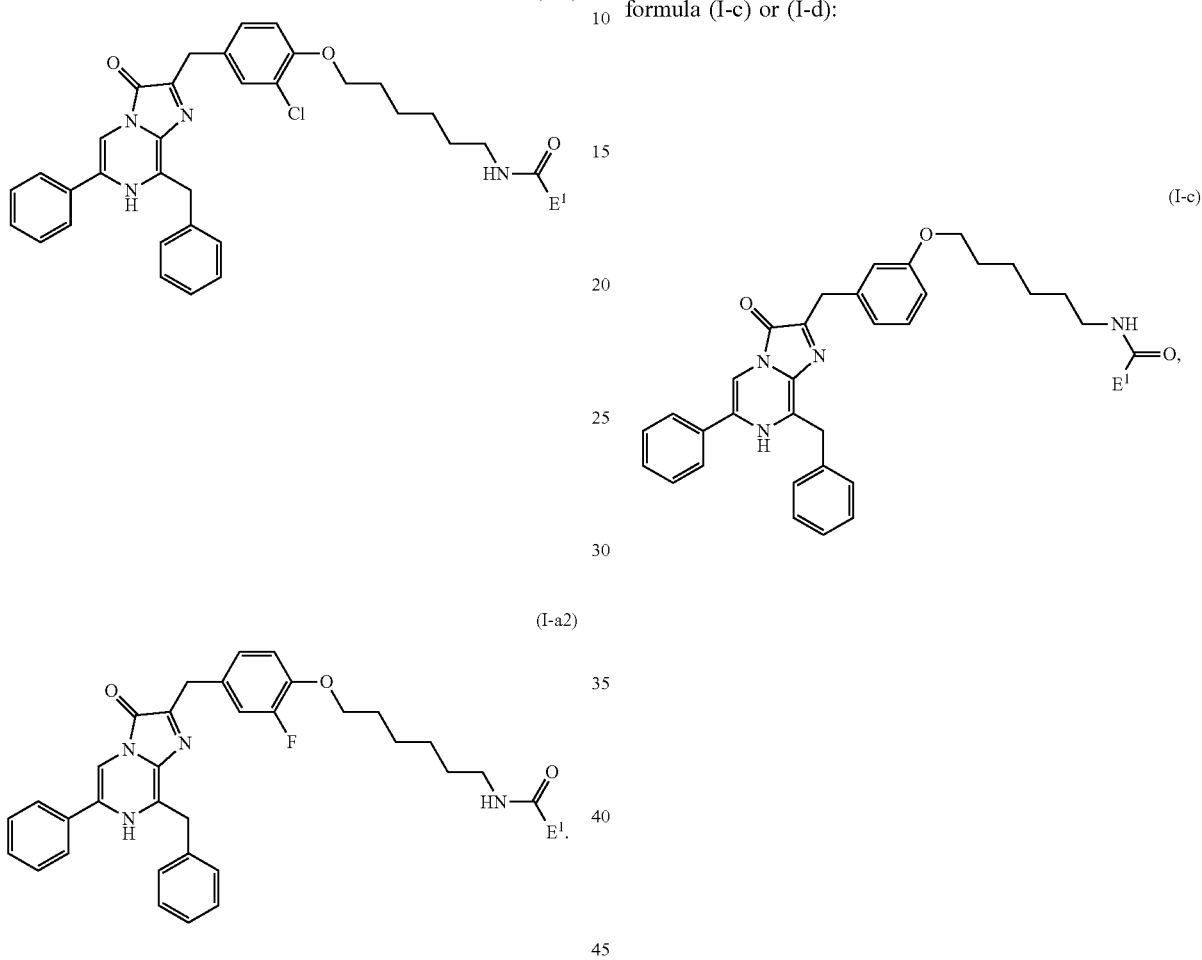

In certain embodiments, the compound of formula (I) has formula (I-b):

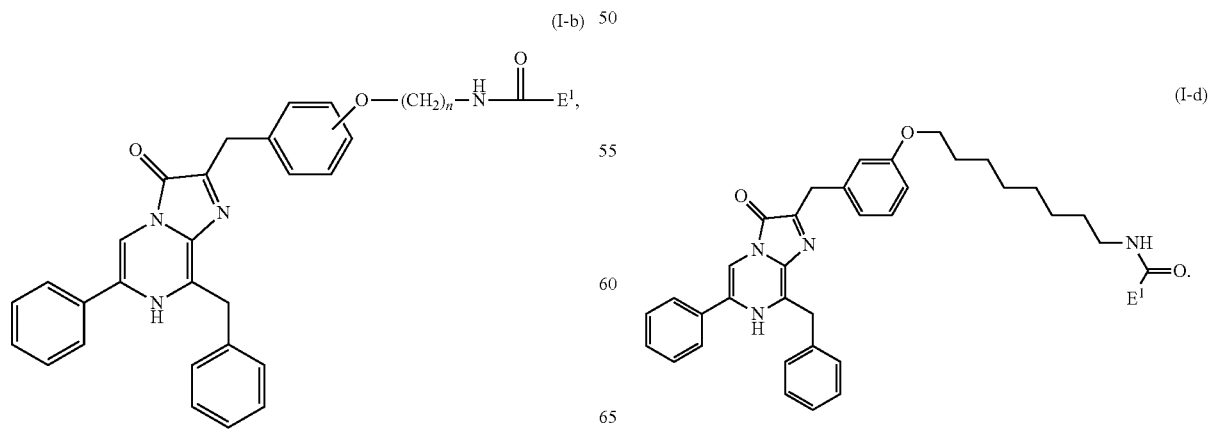

In certain embodiments, the compound of formula (I) is
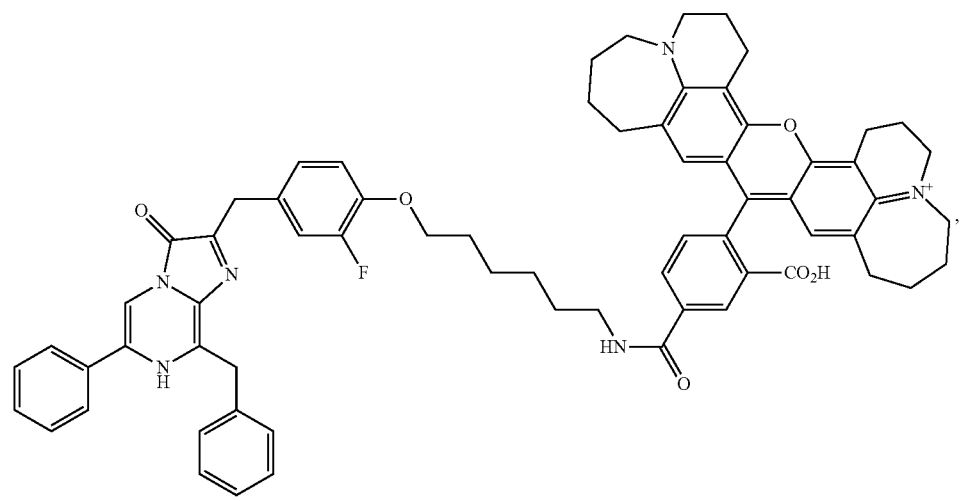
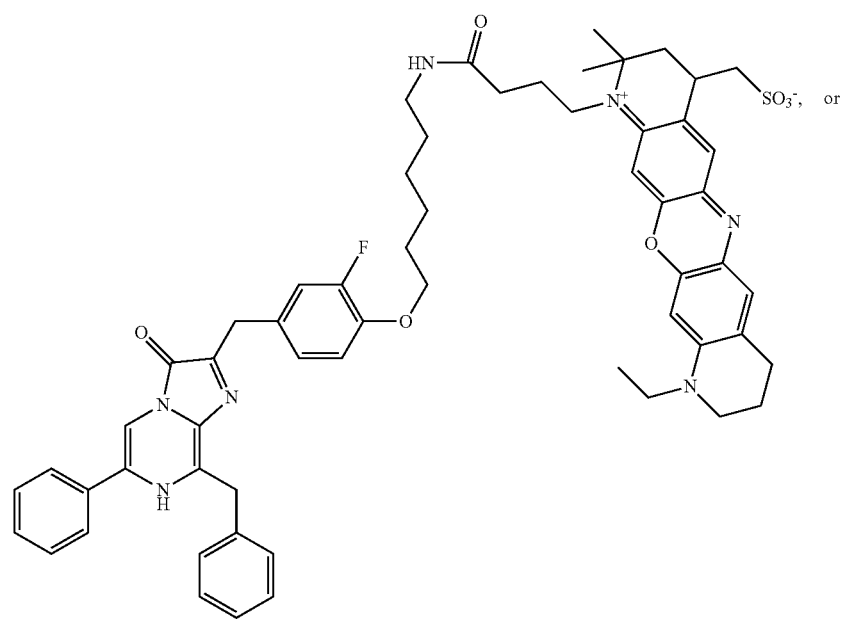
TAK-0052

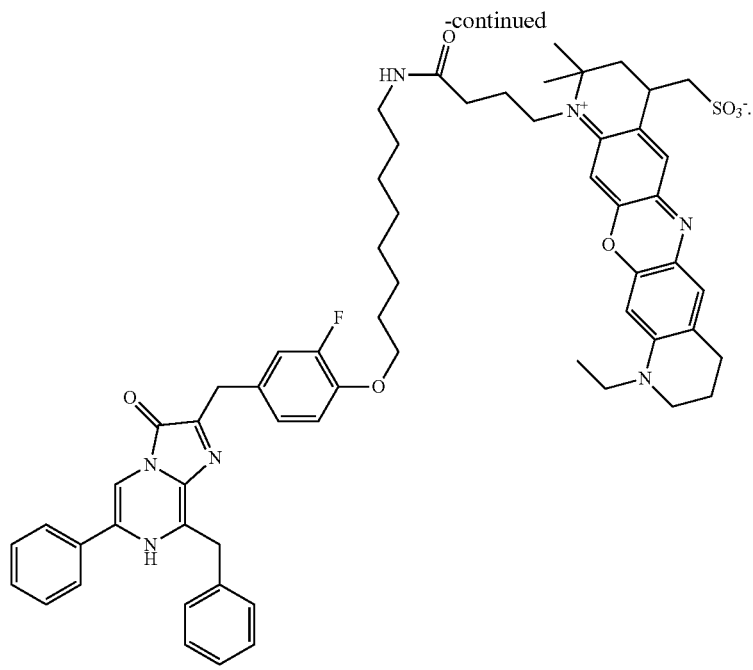

In certain embodiments, the compound of formula (I) is TAK-0043:

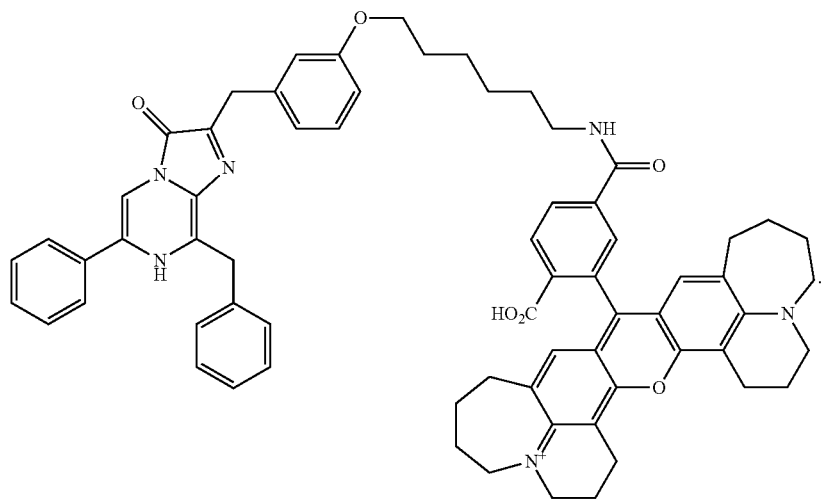

TAK-0043

Compound names are assigned by using Struct=Name naming algorithm as part of CHEMDRAW® ULTRA v. 12.0.

The compounds may exist as stereoisomers wherein asymmetric or chiral centers are present. The stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof, and these are specifically included within the scope of this invention. Stereoisomers include enantiomers and diastereomers and mixtures of enantiomers or diastereomers.

Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography, and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns, or (3) fractional recrystallization methods.

It should be understood that the compounds may possess tautomeric forms, as well as geometric isomers, and that these also constitute an aspect of the invention.

The present disclosure also includes isotopically-labeled compounds, which are identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to, $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

A. Properties of the Compounds of Formula (I)

The compounds of formula (I) may be substrates of luciferases to produce luminescence. "Luminescence" refers to the light output of a luciferase under appropriate conditions, e.g., in the presence of a suitable substrate such as a coelenterazine analogue. The light output may be measured as an instantaneous or near-instantaneous measure of light output (which is sometimes referred to as "T=0" luminescence or "flash") at the start of the luminescence reaction, which may be initiated upon addition of the coelenterazine substrate. The luminescence reaction in various embodiments is carried out in a solution. In other embodiments, the luminescence reaction is carried out on a solid support. The solution may contain a lysate, for example from the cells in a prokaryotic or eukaryotic expression system. In other embodiments, expression occurs in a cell-free system, or the luciferase protein is secreted into an extracellular medium, such that, in the latter case, it is not necessary to produce a lysate. In some embodiments, the reaction is started by injecting appropriate materials, e.g., coelenterazine analogue, buffer, etc., into a reaction chamber (e.g., a well of a multiwell plate such as a 96-well plate) containing the luminescent protein. In still other embodiments, the luciferase and/or coelenterazine analogues (e.g., compounds of formula (I)) are introduced into a host and measurements of luminescence are made on the host or a portion thereof, which can include a whole organism or cells, tissues, explants, or extracts thereof. The reaction chamber may be situated in a reading device which can measure the light output, e.g., using a luminometer or photomultiplier. The light output or luminescence may also be measured over time, for example in the same reaction chamber for a period of seconds, minutes, hours, etc. The light output or luminescence may be reported as the average over time, the half-life of decay of signal, the sum of the signal over a period of time, or the peak output. Luminescence may be measured in Relative Light Units (RLUs).

Compounds of formula (I) can have an RLU of greater than or equal to 1, greater than or equal to 2, greater than or equal to 3, greater than or equal to 4, greater than or equal to 5, greater than or equal to 10, greater than or equal to 20, greater than or equal to 30, greater than or equal to 40, greater than or equal to 50, or greater than or equal to 100, relative to coelenterazine or a known coelenterazine analogue.

In a bioluminescent assay, compounds of formula (I) can have greater than or equal to 80%, greater than or equal to 85%, greater than or equal to 90%, or greater than or equal to 95% of their emitted photons shifted to the emission wavelength of the energy acceptor. For example, the energy acceptor may have an emission wavelength of 500-800 nm.

"Biocompatibility" refers to the tolerance of a cell (e.g., prokaryotic or eukaryotic) to a coelenterazine analogue (e.g., compounds of formula (I)). Biocompatibility of a coelenterazine analogue is related to the stress it causes on the host cell.

Enhanced biocompatibility of the coelenterazine analogues (e.g., compounds of formula (I)), may be determined by measuring cell viability and/or growth rate of cells. For example, enhanced biocompatibility of the coelenterazine analogues may be determined by measuring cell viability in the absence of luciferase expression of cells exposed to the coelenterazine analogues compared to native or known coelenterazines to determine how compatible and/or toxic the coelenterazine analogues are to the cells.

In particular, enhanced biocompatibility may be determined using cell viability analysis (e.g., using the CELL-TITER-GLO® Luminescent Cell Viability assay), an apoptosis assay (e.g., using the CASPASE-GLO® assay technology), or another method known in the art. The effect of the compounds of formula (I) on cell viability or apoptosis may be compared to the effect of native or known coelenterazine analogues on cell viability or apoptosis.

Enhanced biocompatibility may also be determined by measuring the effect of the coelenterazine analogues (e.g., compounds of formula (I)) on cell growth or gene expression. For example, enhanced biocompatibility of the compounds of formula (I) may be determined by measuring the cell number after a period of time or by determining the expression of stress response genes in a sample of cells that are exposed to compounds of formula (I) compared to cells exposed to a native or known coelenterazine or no coelenterazine. The effect of the compounds of formula (I) on cell growth or gene expression may be compared to a native or known coelenterazine.

B. Synthesis of Compounds of Formula (I)

Compounds of formula (I) may be prepared by synthetic processes or by metabolic processes. Preparation of the compounds by metabolic processes includes those occurring in the human or animal body (in vivo) or processes occurring in vitro. Suitable synthesis methods may include, for example, those disclosed in U.S. Ser. No. 62/295,363 to Shakhmin et al., "COELENTERAZINE ANALOGUES," filed Feb. 15, 2016, which is incorporated by reference herein in its entirety.

Compounds of formula (I), wherein the groups $R^1$ and q have the meanings as set forth in the Summary section unless otherwise noted, may be synthesized as shown in Scheme 1.

Abbreviations which have been used in the descriptions of the Schemes that follow are: $Ac_2O$ for acetic anhydride; CDI for carbonyldiimidazole; MeOH for methanol; TMG for 1,1,3,3-tetramethylguanidine; and TFA for trifluoroacetic acid.

Scheme 1. Synthesis of the compound of formula (I)

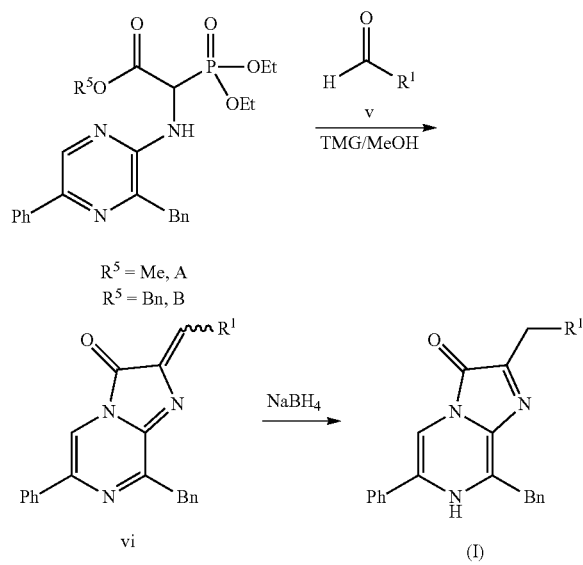

Scheme 1 illustrates the conversion of intermediates A and B to the compound of formula (I), wherein q is 1. Intermediates A and B can be treated with 1,1,3,3-tetramethylguanidine and undergo Horner-Wadsworth-Emmons olefination with aldehyde v, wherein $R^1$ is as defined in the Summary, to yield intermediate vi. Intermediate vi can be reduced to give the compound of formula (I).

Optimum reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration, and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in PGM Wuts and TW Greene, in Greene's book titled Protective Groups in Organic Synthesis (4$^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step) or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material or by resolution of a mixture of the geometric isomers of the compound or intermediates using a standard procedure such as chromatographic separation.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

3. METHODS OF USE AND KITS

The compounds of the disclosure may be used in any way that luciferase substrates, e.g., coelenterazine analogues, have been used. For example, they may be used in a bioluminogenic method that employs an analogue of coelenterazine to detect one or more molecules in a sample, e.g., an enzyme, a cofactor for an enzymatic reaction, an enzyme substrate, an enzyme inhibitor, an enzyme activator, or OH radicals, or one or more conditions, e.g., redox conditions. The sample may include an animal (e.g., a vertebrate), a plant, a fungus, physiological fluid (e.g., blood, plasma, urine, mucous secretions), a cell, a cell lysate, a cell supernatant, or a purified fraction of a cell (e.g., a subcellular fraction). The presence, amount, spectral distribution, emission kinetics, or specific activity of such a molecule may be detected or quantified. The molecule may be detected or quantified in solution, including multiphasic solutions (e.g., emulsions or suspensions), or on solid supports (e.g., particles, capillaries, or assay vessels).

In certain embodiments, the compounds of formula (I) may be used to modify the emission spectra of luminescence generated as a result of reaction with the luciferase enzyme. In some embodiments, the compounds of formula (I) may be tethered by a stable covalent linker to an acceptor molecule which undergoes BRET, shifting the emission spectra of the reaction towards the inherent emission wavelength of the acceptor molecule. Energy acceptors include but are not limited to small molecule fluorescent dyes such as NCT, quenchers, fluorescent particles such as Quantum dots, luminescent metal complexes, and any other known energy acceptors.

In certain embodiments, the compounds of formula (I) may be used to quantify small molecules. In some embodiments, a coelenterazine (e.g., a native or known coelenterazine or a compound of formula (I)) can be used as a probe of a specific biochemical activity, e.g., apoptosis or drug metabolism. In some embodiments, the coelenterazine concentration is coupled to a specific enzyme activity by a "pro-coelenterazine" or "pro-substrate" that can be acted on by the specific enzyme of interest. In some embodiments, the pro-coelenterazine is a molecule that cannot support luminescence directly when combined with a luciferase, but can be converted into coelenterazine through catalytic processing by a specific enzyme of interest. In some embodiments, the approach can be used for enzymes such as those used in drug metabolism, e.g., cytochrome P450 enzymes, monoamine oxidase, and glutathione S-transferase; and apoptosis, e.g., caspases. For example, coelenterazine (e.g., a native or known coelenterazine, or a compound of formula (I)) can be modified to contain a cleavable group, such as 6'-O-methyl. In some embodiments, when incubated with a specific cytochrome P450 enzyme, the 6'O-methyl is cleaved, and the pro-coelenterazine converted to coelenterazine, which can be detected with a luciferase. In some embodiments, the pro-coelenterazine can be combined with other components necessary to support luminescence, e.g., luminescent protein such as a luciferase, to provide a single reagent and a homogeneous assay. For example, when the reagent is added to a sample, luminescence is generated as pro-coelenterazine is converted to coelenterazine. In various embodiments, similar assays can be developed for other enzymes, small molecules, or other cellular processes that can be linked to the generation of coelenterazines from pro-coelenterazines.

In certain embodiments, the compounds of formula (I) can be used for detecting luminescence in live cells. In some embodiments, a luciferase can be expressed in cells (as a reporter or otherwise), and the cells treated with a coelenterazine (e.g., a compound of formula (I)), which will permeate cells in culture, react with the luciferase and generate luminescence. In addition to being cell permeant, the compounds of formula (I) show comparable biocompatibility to native coelenterazine in terms of cell viability. In some embodiments, the compounds of formula (I) containing chemical modifications known to increase the stability of native coelenterazine in media can be synthesized and used for more robust, live cell luciferase-based reporter assays. In still other embodiments, a sample (including cells, tissues, animals, etc.) containing a luciferase and a compound of formula (I) may be assayed using various microscopy and imaging techniques. In still other embodiments, a secretable luciferase is expressed in cells as part of a live-cell reporter system.

In certain embodiments, the compounds of formula (I) disclosed herein may be provided as part of a kit. In some embodiments, the kit may include one or more luciferases (in the form of a polypeptide, a polynucleotide, or both) and a coelenterazine, along with suitable reagents and instructions to enable a user to perform assays such as those disclosed herein. The coelenterazine may be any of the native, known, or compounds of formula (I) disclosed herein. The kit may also include one or more buffers, such as those disclosed herein.

4. EXAMPLES

Example 1. General Synthesis

General Procedure for Method I:

In a 20 mL vial, is placed methyl 2-((3-benzyl-5-phenylpyrazin-2-yl)amino)-2-(diethoxyphosphoryl)acetate (A) (1 eq.), aldehyde (v) (1.1 eq.), and 12 mL of methanol. To that solution, 1,1,3,3-tetramethylguanidine (3 eq.) is added. The reaction mixture is stirred at room temperature until it reaches maximum conversion (2-6 hours). The progress of the reaction is monitored by LCMS. The mixture is poured into water, extracted with ethyl acetate, and dried over $MgSO_4$. The drying agent is filtered off, and the solvent is concentrated under reduced pressure. The residue is subjected to flash chromatography on silica gel using dichloromethane as eluent. The corresponding dehydrocoelenterazine with the general structure vi is isolated and used in the next step without further purification.

Dehydrocoelenterazine vi is dissolved in 25 mL of dichloromethane and 10 mL of methanol and cooled to 0° C. To this solution, $NaBH_4$ (3 eq.) is added, and the reaction mixture stirred at 0° C. for 30 minutes. The reaction mixture is quenched with the 50 mL of 0.1 M HCl, extracted with dichloromethane, and dried over $MgSO_4$. The drying agent is filtered off, the solvent is concentrated under reduced pressure, and the residue is purified on silica gel using dichloromethane/methanol as eluent. The target coelenterazine analogue is isolated and dried on high vacuum.

Example 2. Synthesis of TAK-0043

TAK-0043 was prepared as described below.

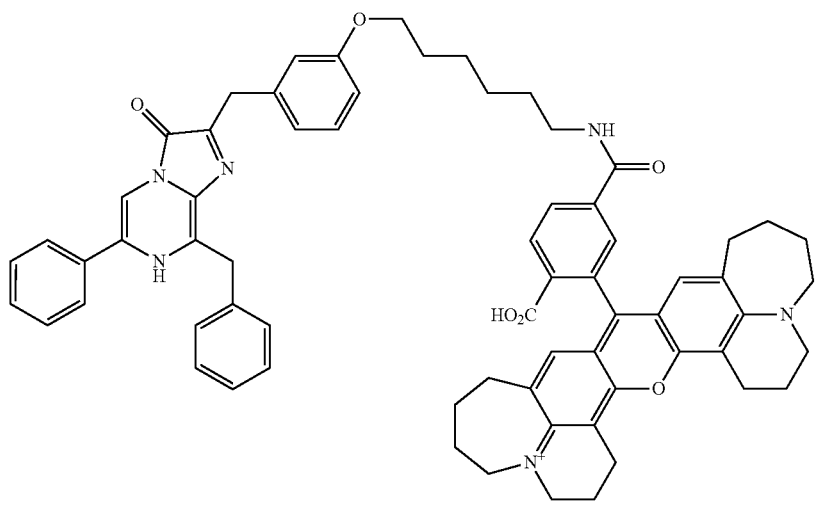

TAK-0043

Example 2A. Tert-butyl (6-(3-formylphenoxy)hexyl)carbamate

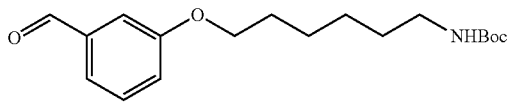 [SMILES: CC(C)(C)OC(=O)NCCCCCCOc1cccc(C=O)c1]

To a suspension of NaH (0.2 g) in DMF (40 mL), 3-hydroxybenzaldehyde (0.5 g) was added. After stirring for 2 h, N-Boc-6-Bromohexylamine (1.2 g) was added, and the reaction stirred overnight. The reaction was then partitioned between water and EtOAc, the layers separated, the organic layer washed with water and brine, dried, and concentrated. The resulting brown oil was purified by silica gel chromatography with a gradient of EtOAc in heptanes to provide the title compound (0.8 g, 61%) as a brown oil: $^1$H NMR (300 MHz, DMSO-$d_6$) δ=9.95 (s, 1H), 7.52-7.45 (m, 2H), 7.40-7.39 (m, 1H), 7.28-7.23 (m, 1H), 6.74 (t, J=5.5, 1H), 4.01 (t, J=6.5, 2H), 2.89 (q, J=7.4, 2H), 1.75-1.66 (m, 2H), 1.44-1.22 (m, 15H); ESI-MS (m/z) [M+H] (C18H27NO4) observed 322.

Example 2B. Tert-butyl (6-(3-((8-benzyl-3-oxo-6-phenyl-3,7-dihydroimidazo[1,2-a]pyrazin-2-yl)methyl)phenoxy)hexyl)carbamate

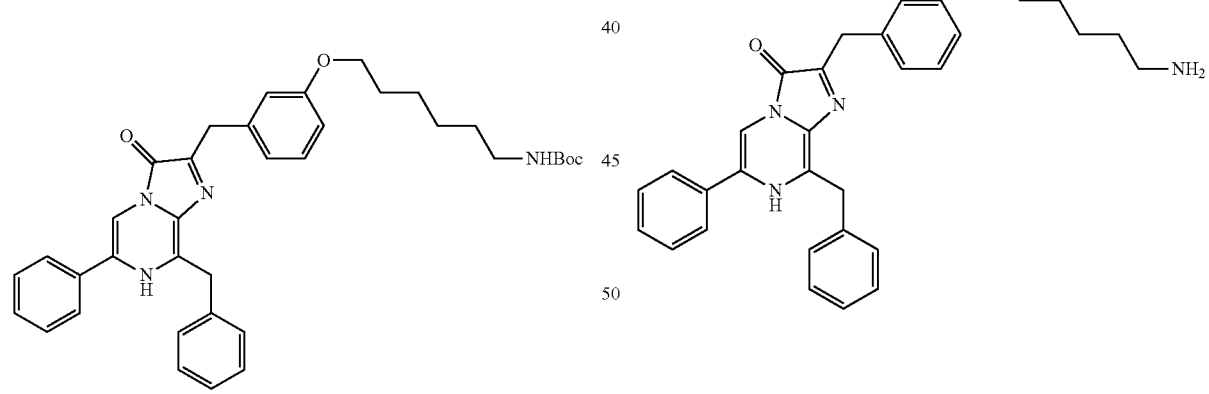

To a solution of benzyl 2-((3-benzyl-5-phenylpyrazin-2-yl)amino)-2-(diethoxyphosphoryl)acetate (prepared according to the method disclosed in U.S. Ser. No. 62/295,363, 0.3 g) in MeOH (15 mL), tert-butyl (6-(3-formylphenoxy)hexyl) carbamate (0.2 g) and tetramethylguanidine (0.9 mL) was added. The reaction was stirred for 20 min, then partitioned between EtOAc and water. The layers were separated, the organic layer washed with brine, dried, and concentrated. The resulting red solid was purified by silica gel with a gradient of MeOH in CH$_2$Cl$_2$ to provide partially purified dehydrocoelenterazine as a red solid, which was carried on without further purification. This red solid was dissolved in CH$_2$Cl$_2$/MeOH (1/1, 5 mL) and treated with excess NaBH$_4$. After stirring for 30 min, the solution was quenched with water, extracted with CH$_2$Cl$_2$, dried, and concentrated. The resulting coelenterazine was purified on silica gel with a gradient of MeOH in CH$_2$Cl$_2$ to provide the title compound (0.15 g, 45%) as an orange oil: $^1$H NMR (300 MHz, CD$_2$Cl$_2$) δ=7.48-7.45 (m, 4H), 7.31-7.22 (m, 9H), 7.06 (br s, 1H), 6.86 (br s, 2H), 6.62 (br s, 1H), 4.69 (s, 2H), 4.40 (s, 2H), 4.08 (s, 2H), 3.81 (br s, 2H), 3.00 (q, J=6.4, 2H), 1.66 (s, 2H), 1.45-1.27 (m, 20H).

Example 2C. 2-(3-((6-Aminohexyl)oxy)benzyl)-8-benzyl-6-phenylimidazo[1,2-a]pyrazin-3(7H)-one To a solution of tert-butyl (6-(3-((8-benzyl-3-oxo-6-phenyl-3,7-dihydroimidazo[1,2-a]pyrazin-2-yl)methyl)phenoxy)hexyl)carbamate (0.14 g) in CH$_2$Cl$_2$ (15 mL), TFA (1 mL) was added. The orange solution was stirred for 1 hr, then toluene was added, and the solution concentrated to provide the title compound as an amber glass (0.09 g, 80%): ESI MS (m/z) [M+H] (C$_{32}$H$_{34}$N$_4$O$_2$) found 507.2.

Example 2D. TAK-0043

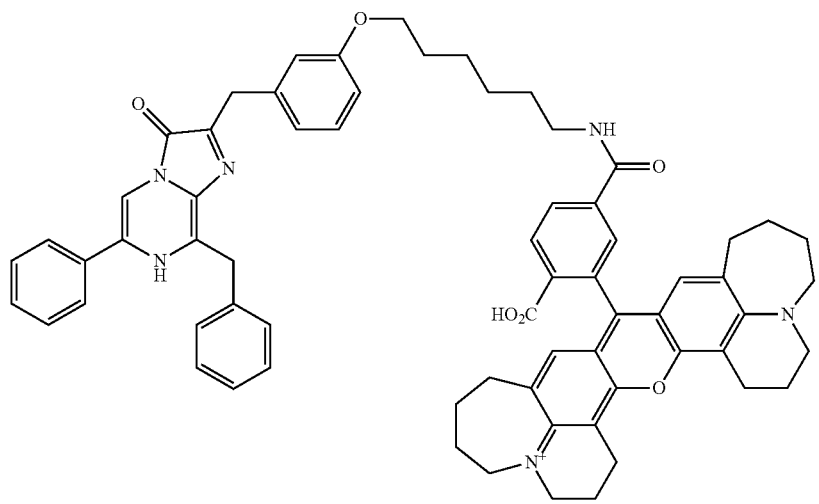 [SMILES: O=C(NCCCCCCOc1cccc(Cc2nc3c(Cc4ccccc4)[nH]c(-c4ccccc4)cn-3c2=O)c1)c1ccc(C(=O)O)c(C2=c3cc4c5c(c3Oc3c2cc2c6c3CCCN6CCCC2)CCC[N+]=5CCCC4)c1]

To a solution of 2-(3-((6-aminohexyl)oxy)benzyl)-8-benzyl-6-phenylimidazo[1,2-a]pyrazin-3(7H)-one (5 mg) in MeOH (1 mL), NCT-tetrafluorophenyl ester (5 mg) and collidine (10 μL) was added. The blue solution was stirred for 3 days, after which the reaction was quenched with dilute aqueous TFA, and the resulting solution purified by preparative HPLC with ACN as the mobile phase. The title compound was isolated as a blue solid (0.5 mg, 5%): TOF-HRMS (m/z) [M+] ($C_{67}H_{66}N_6O_6$) found 1051.5135.

Example 3. Synthesis of Dye-Linked Compound

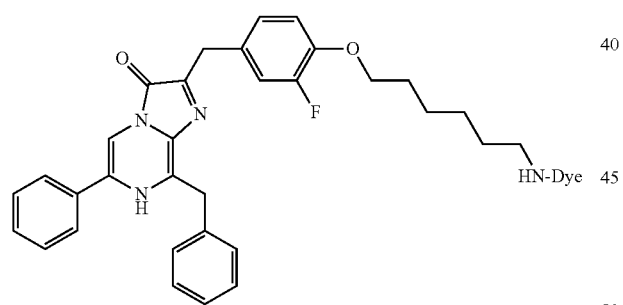

Example 3A. Tert-butyl (6-(2-fluoro-4-formylphenoxy)hexyl)carbamate (JRW-0797)

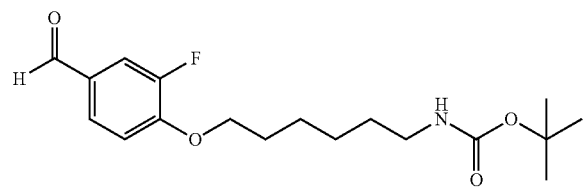 [SMILES: CC(C)(C)OC(=O)NCCCCCCOc1ccc(C=O)cc1F]

To a solution of 3-fluoro-4-hydroxybenzaldehyde (200 mg, 1.43 mmol) in acetonitrile (20 mL), tert-butyl (6-bromohexyl)carbamate (400 mg, 1.43 mmol) and cesium carbonate (558 mg, 1.71 mmol) was added and heated to 75° C. for 18 h. The reaction mixture was diluted with ethyl acetate and water. The organic layer was washed with $NaHCO_3$ (sat), dried with sodium sulfate, filtered, and concentrated to yield a dark brown oil (470 mg, crude): ESI-MS (m/z) [M+H] ($C_{18}H_{26}FNO_4$) observed 340.

Example 3B. Tert-butyl (Z)-(6-(4-((8-benzyl-3-oxo-6-phenylimidazo[1,2-a]pyrazin-2(3H)-ylidene)methyl)-2-fluorophenoxy)hexyl)carbamate (JRW-0798)

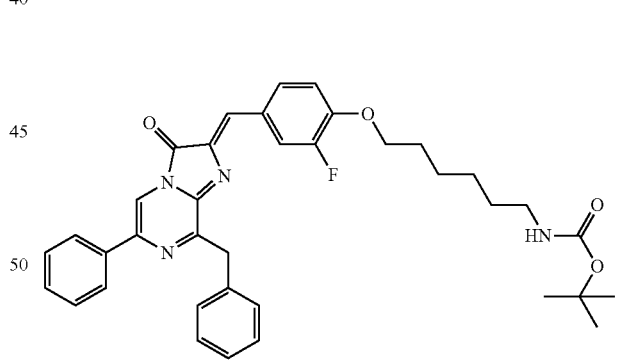

To a solution of methyl 2-((3-benzyl-5-phenylpyrazin-2-yl)amino)-2-(diethoxyphosphoryl)acetate (200 mg, 0.43 mmol) and tert-butyl (6-(2-fluoro-4-formylphenoxy)hexyl)carbamate (216 mg, 0.64 mmol) in methanol (5 mL), tetramethylguanidine (147 mg, 1.3 mmol) was added. The mixture stirred for 30 min. The reaction was diluted with dichloromethane and poured into weakly acidic water (HCl). The layers were separated, and the aqueous layer was extracted with dichloromethane. The organic layers were combined, dried with sodium sulfate, filtered, and concentrated. The crude product was chromotgraphed (DCM/MeOH) to give a black solid (250 mg, crude).

Example 3C. Tert-butyl (6-(4-((8-benzyl-3-oxo-6-phenyl-3,7-dihydroimidazo[1,2-a]pyrazin-2-yl)methyl)-2-fluorophenoxy)hexyl)carbamate (JRW-0799)

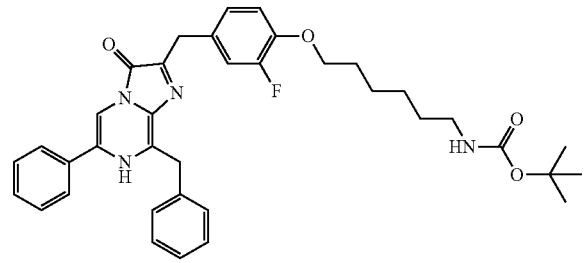 [SMILES: CC(C)(C)OC(=O)NCCCCCCOc1ccc(Cc2nc3c(Cc4ccccc4)[nH]c(-c4ccccc4)cn-3c2=O)cc1F]

A solution of tert-butyl (Z)-(6-(4-((8-benzyl-3-oxo-6-phenylimidazo[1,2-a]pyrazin-2(3H)-ylidene)methyl)-2-fluorophenoxy)hexyl)carbamate (250 mg, 0.40 mmol) in methanol/dichloromethane (1:1, 10 mL) was chilled to 0° C. Sodium borohydride (75 mg, 2.0 mmol) was added. The reaction stirred for 30 min. The reaction was diluted with dichloromethane and poured into weakly acidic water (HCl). The layers were separated, and the aqueous layer was extracted with dichloromethane. The organic layers were combined, dried with sodium sulfate, filtered, and concentrated. The crude product was chromotgraphed (DCM/MeOH) to give an orange solid (108 mg, 40% over two steps): ESI-MS (m/z) [M+H]($C_{37}H_{41}FN_4O_4$) observed 625.

Example 3D. 2-(4-((6-Aminohexyl)oxy)-3-fluorobenzyl)-8-benzyl-6-phenylimidazo[1,2-a]pyrazin-3(7H)-one (JRW-0801)

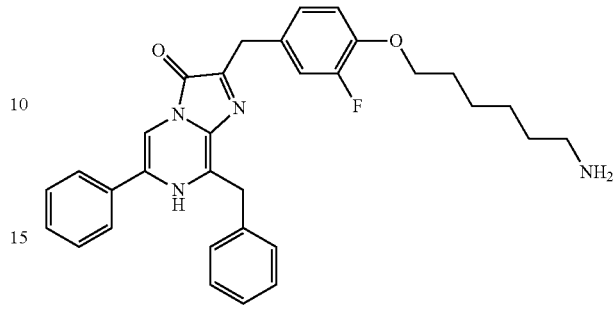

To a solution of tert-butyl (6-(4-((8-benzyl-3-oxo-6-phenyl-3,7-dihydroimidazo[1,2-a]pyrazin-2-yl)methyl)-2-fluorophenoxy)hexyl)carbamate (108 mg, 0.17 mmol) dissolved in dichloromethane (10 mL), trifluoroacetic acid (1 mL) was added. The mixture stirred for 1 h. The reaction was diluted with toluene and concentrated. Additional toluene was added and concentrated again (2×) giving a red foam. The crude product was dissolved in methanol, and Celite was added. The suspension was concentrated and the powder was chromatographed (DCM/MeOH) to give a red orange foam (110 mg, quant): $^1$H NMR (300 MHz, $CD_3OD$) δ 7.81-7.58 (m, 3H), 7.56-7.37 (m, 5H), 7.35-7.19 (m, 3H), 7.16-6.93 (m, 3H), 4.42 (s, 2H), 4.10 (s, 2H), 4.01 (t, J=6.2, 2H), 2.99-2.85 (m, 2H), 1.92-1.39 (m, 8H); ESI-MS (m/z) [M+H] ($C_{32}H_{33}FN_4O_2$) observed 525; HPLC 99.3% (AUC), $T_R$ 4.12 min; UV (MeOH) λ 433 nm, ε 6091.

Example 3E. Dye-Linked Compound

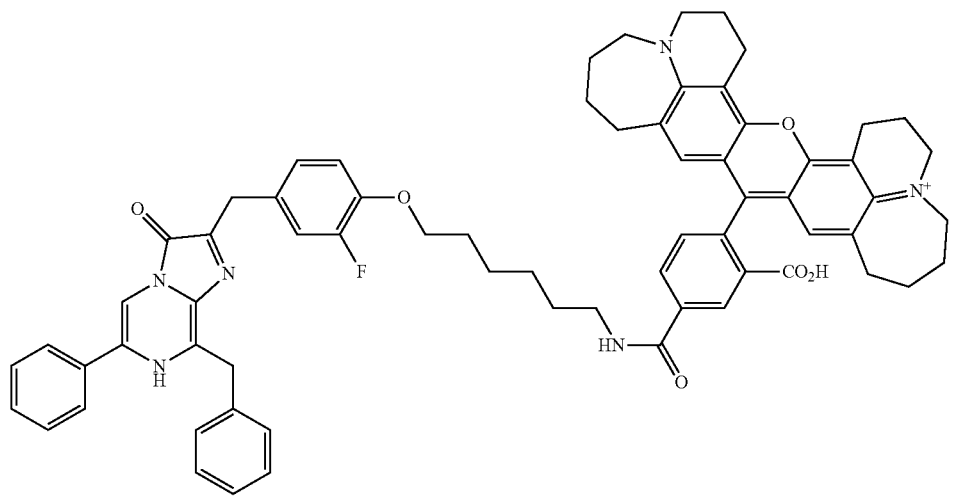 [SMILES: O=C(NCCCCCCOc1ccc(Cc2nc3c(Cc4ccccc4)[nH]c(-c4ccccc4)cn-3c2=O)cc1F)c1ccc(C2=c3cc4c5c(c3Oc3c2cc2c6c3CCCN6CCCC2)CCC[N+]=5CCCC4)c(C(=O)O)c1]

The synthesis of the NCT conjugated coelenterazine depicted above can be carried out in a manner similar to the synthesis of TAK-0043 (described above) using NCT-TFP and the amine from Example 3D. Similarly, other amine reactive dye species can be coupled to the amine from Example 3D to generate analogous coelenterazine dye conjugates.

Example 3F. (1-(4-((6-(4-((8-benzyl-3-oxo-6-phenyl-3,7-dihydroimidazo[1,2-a]pyrazin-2-yl)methyl)-2-fluorophenoxy)hexyl)amino)-4-oxobutyl)-11-ethyl-2,2-dimethyl-3,4,8,9,10,11-hexahydro-2H-dipyrido[3,2-b:2',3'-i]phenoxazin-1-ium-4-yl) methanesulfonate (TAK-0052)

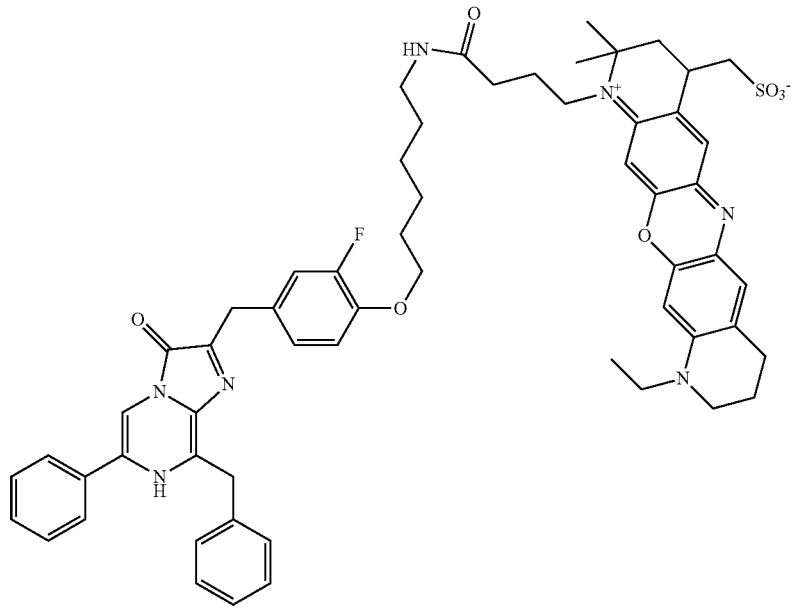

To a solution of 2-(4-((6-Aminohexyl)oxy)-3-fluorobenzyl)-8-benzyl-6-phenylimidazo[1,2-a]pyrazin-3(7H)-one (3 mg, 0.006 mmol) and Atto 655 SE (3.5 mg, 0.006 mmol) in CH2Cl2/EtOH (4 mL), collidine (0.1 mL) was added. The mixture stirred for 3 h. The reaction was quenched with dilute aqueous TFA, and the resulting solution purified by preparative HPLC with ACN as the mobile phase. The title compound was isolated as a blue solid (5 mg, 85%): TOF-HRMS (m/z) [M+] ($C_{59}H_{64}FN_7O_7S$) found 1034.4633.

Example 4. Synthesis of Dye-Linked Compound

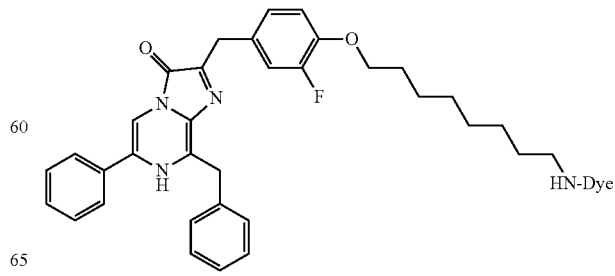

Example 4A. tert-butyl (8-(2-fluoro-4-formylphenoxy)octyl)carbamate (JRW-0898)

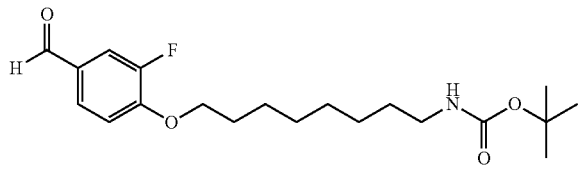 [SMILES: CC(C)(C)OC(=O)NCCCCCCCCOc1ccc(C=O)cc1F]

Step 1. tert-butyl (8-hydroxyoctyl)carbamate (JRW-0896)

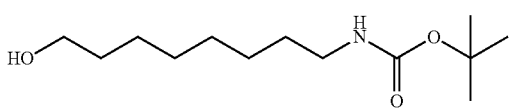 [SMILES: CC(C)(C)OC(=O)NCCCCCCCCO]

To a solution of 8-aminooctan-1-ol (1.0 g, 6.9 mmol) in THF (20 mL) was added sodium bicarbonate (saturated solution, 10 mL) and di-tert-butyl dicarbonate (1.8 g, 8.3 mmol). The reaction mixture was stirred overnight at rt, then diluted with ethyl acetate and water. The layers were separated and the aqueous layer extracted with ethyl acetate. The organic layers were combined, dried with sodium sulfate, filtered, and concentrated. The crude product was chromotgraphed (DCM/MeOH) to give a white solid (1.6 g, 94%):

$^1$H NMR (400 MHz, CDCl$_3$) δ 4.51 (s, 1H), 3.66 (t, J=6.6 Hz, 2H), 3.18-3.08 (m, 2H), 1.66-1.53 (m, 2H), 1.46 (s, 11H), 1.43-1.26 (m, 8H).

Step 2. tert-butyl (8-(2-fluoro-4-formylphenoxy)octyl)carbamate (JRW-0898)

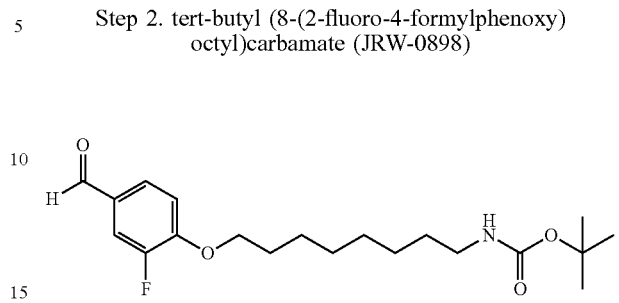

To a solution of 3-fluoro-4-hydroxybenzaldehyde (0.91 g, 6.5 mmol) in THF (20 mL), tert-butyl (8-hydroxyoctyl)carbamate (1.60 g, 6.5 mmol), triphenylphosphine (1.88 g, 7.2 mmol) and isopropyl 2-(isobutyryloxy)diazene-1-carboxylate (1.45 g, 7.2 mmol) dropwise was added. The reaction stirred at rt for 7 h then diluted with ethyl acetate and water. The layers were separated, and the aqueous layer extracted with ethyl acetate. The organic layers were combined, dried with sodium sulfate, filtered, and concentrated. The crude product was a white solid (2.1 g): $^1$H NMR (400 MHz, CDCl$_3$) δ 9.87 (d, J=2.1 Hz, 1H), 7.69-7.56 (m, 2H), 7.07 (t, J=8.1 Hz, 1H), 4.52 (s, 1H), 4.13 (t, J=6.5 Hz, 2H), 3.18-3.07 (m, 2H), 1.94-1.76 (m, 2H), 1.57-1.42 (m, 13H), 1.42-1.30 (m, 6H).

Example 4B. tert-butyl (Z)-(8-(4-((8-benzyl-3-oxo-6-phenylimidazo[1,2-a]pyrazin-2(3H)-ylidene)methyl)-2-fluorophenoxy)octyl)carbamate (TAK-0055)

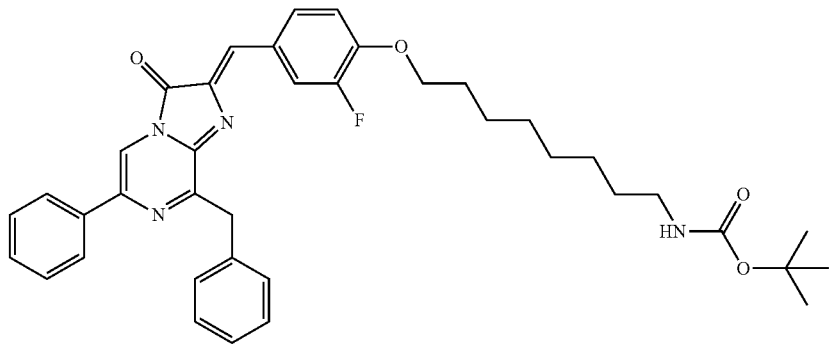 [SMILES: CC(C)(C)OC(=O)NCCCCCCCCOc1ccc(/C=C2\N=C3C(Cc4ccccc4)=NC(c4ccccc4)=CN3C2=O)cc1F]

To a solution of methyl 2-((3-benzyl-5-phenylpyrazin-2-yl)amino)-2-(diethoxyphosphoryl)acetate (230 mg, 0.49 mmol) and tert-butyl (8-(2-fluoro-4-formylphenoxy)octyl)carbamate (200 mg, 0.54 mmol) in methanol (10 mL), tetramethylguanidine (170 mg, 1.5 mmol) was added. The mixture stirred for 30 min. The reaction was diluted with dichloromethane and poured into weakly acidic water (HCl). The layers were separated, and the aqueous layer was extracted with dichloromethane. The organic layers were combined, dried with sodium sulfate, filtered, and concentrated. The crude product was chromotgraphed (DCM/MeOH) to give a red solid (360 mg, crude).

Example 4C. tert-butyl (8-(4-((8-benzyl-3-oxo-6-phenyl-3,7-dihydroimidazo[1,2-a]pyrazin-2-yl)methyl)-2-fluorophenoxy)octyl)carbamate (TAK-0056)

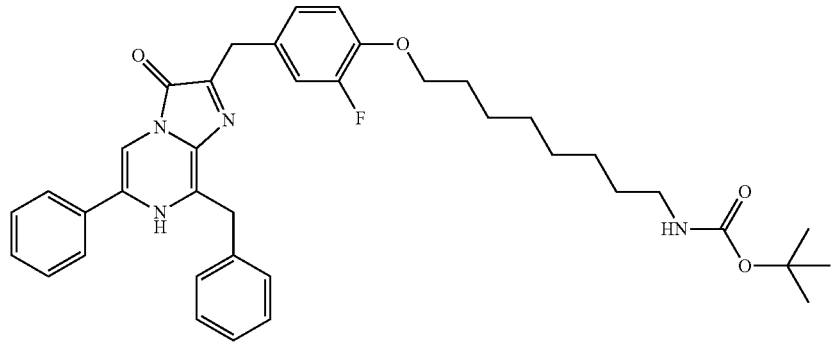 [SMILES: CC(C)(C)OC(=O)NCCCCCCCCOc1ccc(Cc2nc3c(Cc4ccccc4)[nH]c(-c4ccccc4)cn-3c2=O)cc1F]

A solution of tert-butyl (Z)-(8-(4-((8-benzyl-3-oxo-6-phenylimidazo[1,2-a]pyrazin-2(3H)-ylidene)methyl)-2-fluorophenoxy)octyl)carbamate (310 mg, 0.48 mmol) in methanol/dichloromethane (1:1, 20 mL) was chilled to 0° C. Sodium borohydride (90 mg, 2.4 mmol) was added. The reaction stirred for 50 min. The reaction was diluted with dichloromethane and poured into weakly acidic water (HCl). The layers were separated, and the aqueous layer was extracted with dichloromethane. The organic layers were combined, dried with sodium sulfate, filtered, and concentrated. The crude product was chromotgraphed (DCM/MeOH) to give an orange solid (280 mg, 95% over two steps): ESI-MS (m/z) [M+H]($C_{39}H_{45}FN_4O_4$) observed 652.

Example 4D. 2-(4-((8-aminooctyl)oxy)-3-fluorobenzyl)-8-benzyl-6-phenylimidazo[1,2-a]pyrazin-3(7H)-one (TAK-0057)

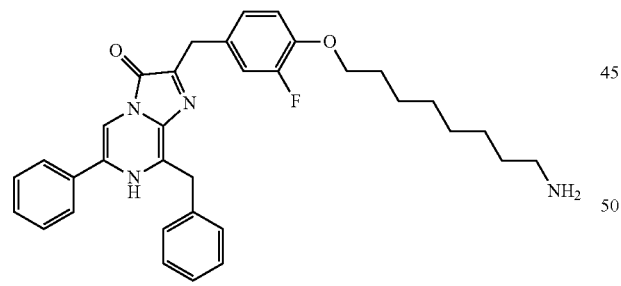

To a solution of tert-butyl (6-(4-((8-benzyl-3-oxo-6-phenyl-3,7-dihydroimidazo[1,2-a]pyrazin-2-yl)methyl)-2-fluorophenoxy)octyl)carbamate (280 mg, 0.43 mmol) dissolved in dichloromethane (15 mL), trifluoroacetic acid (1 mL) was added. The mixture stirred for 1 h. The reaction was diluted with toluene and concentrated. Additional toluene was added and concentrated again (2×) giving a brown gum. The crude product was dissolved in acetonitrile, and the resulting solution purified by preparative HPLC with ACN as the mobile phase. Product was isolated as a yellow solid (170 mg, 71%): $^1$H NMR (400 MHz, CD$_3$OD) δ 7.88 (s, 1H), 7.71-7.68 (m, 2H), 7.51-7.42 (m, 5H), 7.32 (t, J=7.3 Hz, 2H), 7.25 (t, J=7.3 Hz, 1H), 7.13-7.05 (m, 2H), 6.98 (t, J=8.4 Hz, 1H), 4.47 (s, 2H), 4.14 (s, 2H), 4.00 (t, J=5.8 Hz, 2H), 2.92 (t, J=8.0 Hz, 2H), 1.81-1.74 (m, 2H), 1.70-1.62 (m, 2H), 1.54-1.47 (m, 2H), 1.43-1.40 (m, 6H); $^{13}$C NMR (100 MHz, CD$_3$OD) δ 153.6, 151.2, 145.7, 145.6, 136.3, 132.5, 131.2, 129.4, 128.8, 128.5, 128.4, 126.9, 126.6, 126.5, 124.2, 116.0, 115.8, 114.6, 108.2, 68.9, 39.3, 34.3, 31.2, 28.9, 28.8, 28.7, 27.2, 26.0, 25.6; ESI-MS (m/z) [M+H] ($C_{34}H_{37}FN_4O_2$) observed 553, HRMS observed 553.2954.

Example 4E. (1-(4-(4-((8-(4-((8-benzyl-3-oxo-6-phenyl-3,7-dihydroimidazo[1,2-a]pyrazin-2-yl)methyl)-2-fluorophenoxy)octyl)amino)-4-oxobutyl)-11-ethyl-2,2-dimethyl-3,4,8,9,10,11-hexahydro-2H-dipyrido[3,2-b:2',3'-i]phenoxazin-1-ium-4-yl)methanesulfonate

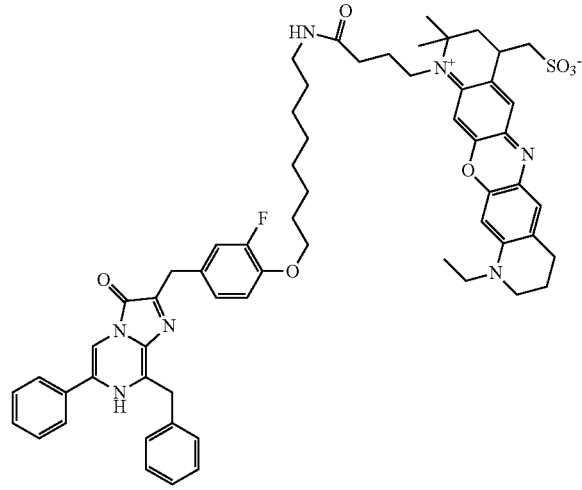

The synthesis of the Atto 655 conjugated coelenterazine depicted above can be carried out in a manner similar to the synthesis of TAK-0043 (described above) using Atto 655 SE and the amine from Example 4D. Similarly, other amine reactive dye species can be coupled to the amine from Example 4D to generate analogous coelenterazine dye conjugates. Exemplary dyes also include other Atto dyes such as Atto 610 and Atto 680, and fluorescein and rhodamine dyes such as Oregon Green or tetramethylrhodamine.

Example 5. Spectral Properties of TAK-0043 and TAK-0052

Figure 2A:
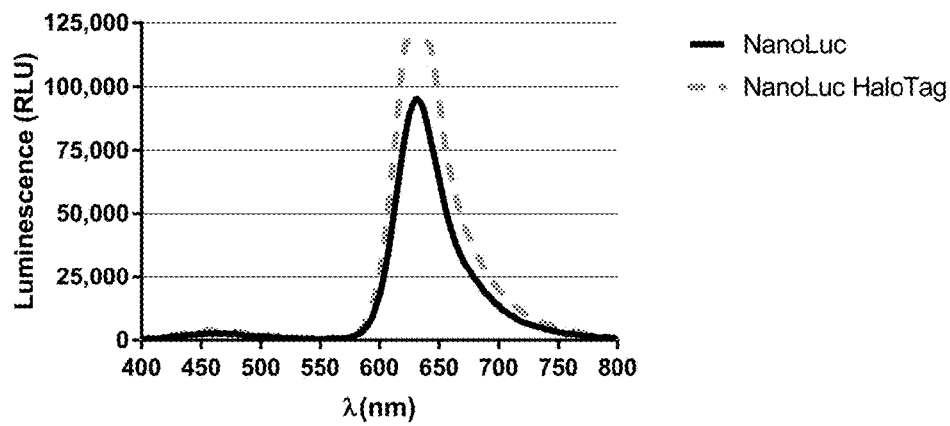
FIGS. 2A-2D show the spectral profiles of varying concentrations of TAK-0043 and enzyme in NanoGlo® buffer. For all concentrations of TAK-0043 and enzyme used, the emission wavelength shows that >95% of the emitted photons are shifted to the NCT dye emission, with a maximum at 618 nm.
Figure 2B:
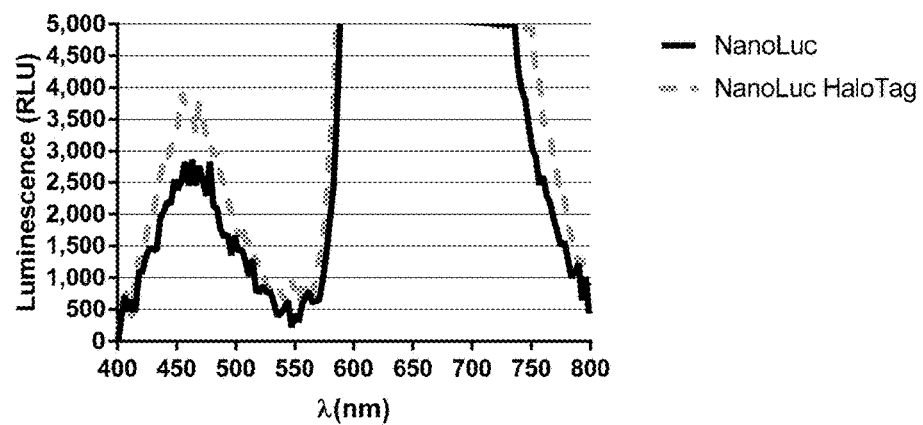
Figure 2C:
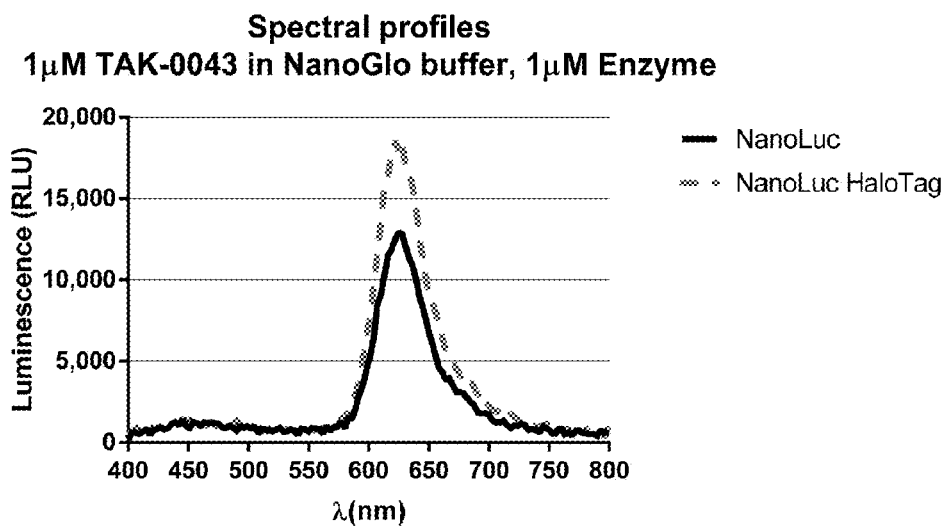
Figure 2D:
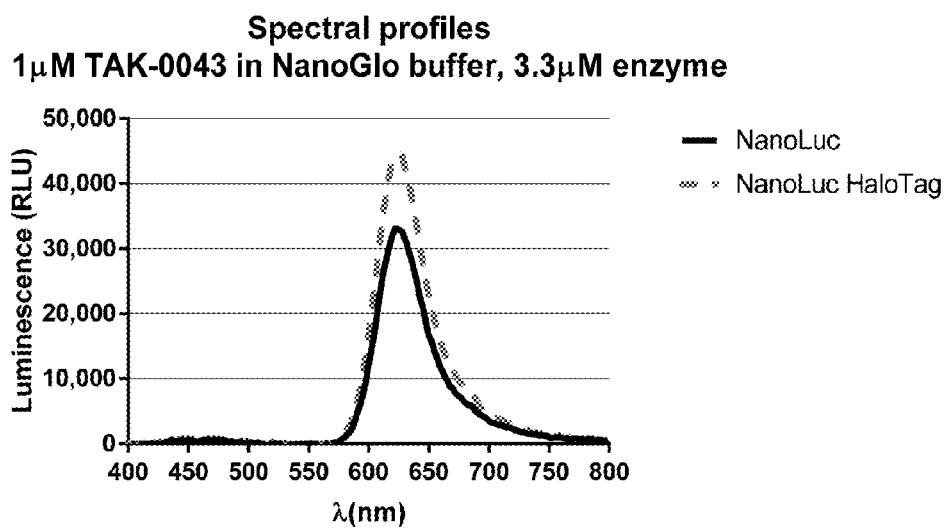

TAK-0043 was tested as a potential coelenterazine analogue capable of shifting the emission spectrum in a coelenterazine/luciferase reaction. A dilution series of purified NanoLuc® enzyme (Promega E499a) and NanoLuc-Halotag fusion protein enzyme was prepared in OptiMEM+ 0.1% FBS starting 2 µM. 50 ul of the 2 µM enzyme dilutions were combined with 50 µl of 2 µM and 20 µM TAK-0043 in NanoGlo® buffer in triplicate. These samples were immediately read on the Tecan-M1000 using 3 nm increments to obtain spectral profiles. The average of the 3 spectral readings is reported in FIGS. 2A-2C. Another spectral measurement was completed by combining 50 µl of 6.6 µM NanoLuc® enzyme and NanoLuc-Halotag fusion protein enzyme in OptiMEM+0.1% FBS with 50 µl of 2 µM TAK-0043 in NanoGlo® buffer in triplicate. This sample was also read on the Tecan M-1000 using 3 nM increments. Results are shown in FIG. 2D. For all concentrations of TAK-0043 and enzyme used, the emission wavelength shows that >95% of the emitted photons are shifted to NCT emission, with a maximum at 618 nm. The peak for coelenterazine emission at 460 nm was nearly invisible.

Figure 3A:
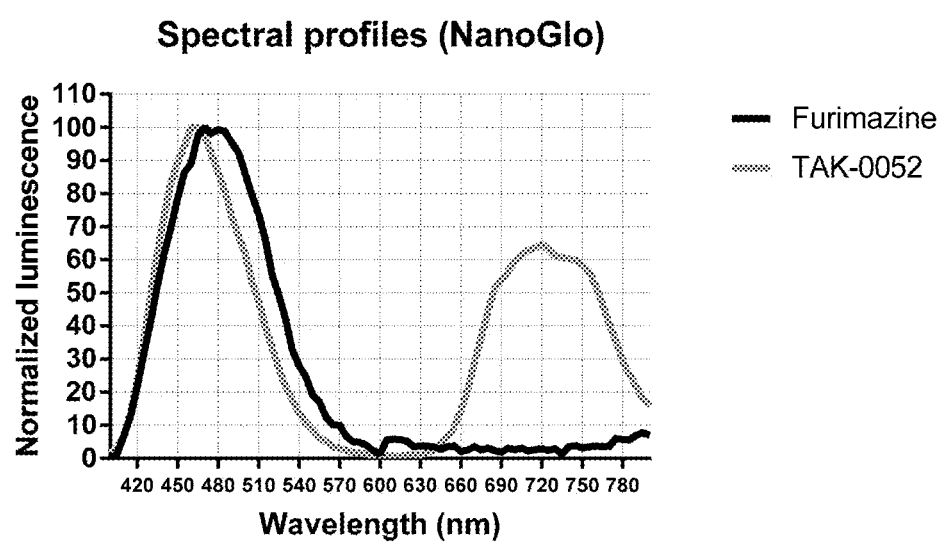
FIG. 3A shows the spectral profiles of furimazine and TAK-0052. Furimazine and TAK-0052 were diluted into NanoGlo® buffer to a concentration of 50 uM. NanoLuc® was diluted into TBS+0.01% BSA to a concentration of 2 µM and 0.2 nM. In triplicate, 50 µl of the 2 µM NanoLuc® sample was combined with 50 µl of TAK-0052 and 50 µl of the 0.2 nM solution was combined in triplicate with 50 µl of the furimazine solution. Spectral profiles were obtained by measuring 3 nm wavelength increments on the Tecan-M1000.

TAK-0052 was tested as a potential coelenterazine analogue capable of shifting the emission spectrum in a coelenterazine/luciferase reaction. Furimazine and TAK-0052 were diluted into NanoGlo® buffer to a concentration of 50 uM. NanoLuc® enzyme was diluted into TBS+0.01% BSA to a concentration of 2 µM and 0.2 nM. In triplicate, 50 µl of the 2 µM NanoLuc® sample was combined with 50 µl of TAK-0052 and 50 µl of the 0.2 nM solution was combined in triplicate with 50 µl of the furimazine solution. Spectral profiles were obtained by measuring 3 nm wavelength increments on the Tecan-M1000. Results are shown in FIG. 3A.

Figure 3B:
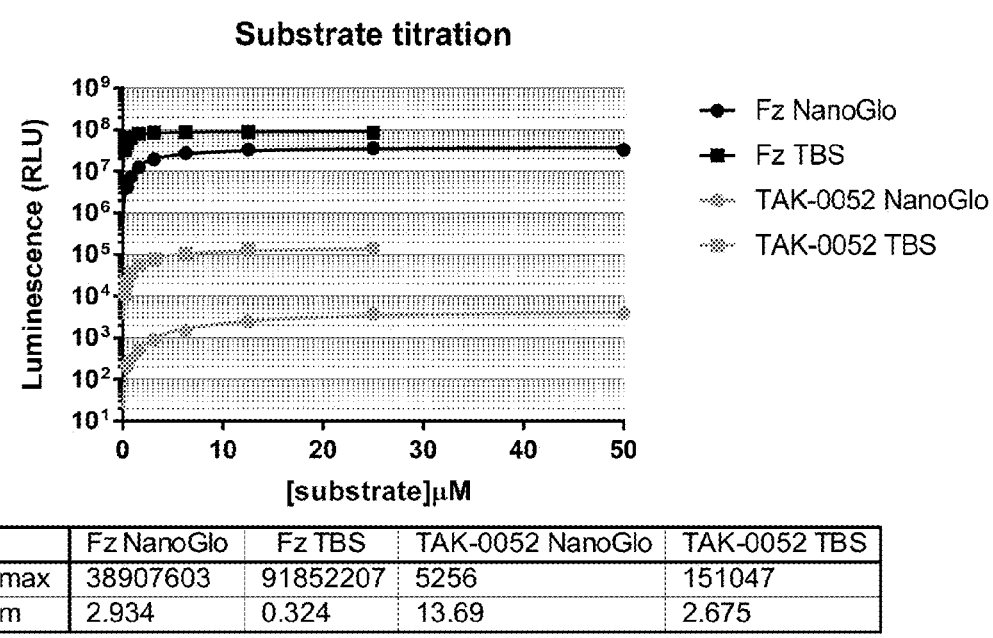
FIG. 3B shows representative results of a substrate titration. Furimazine and TAK-0052 were diluted to 100 µM in NanoGlo® buffer or 50 µM in TBS+0.01% BSA. Two fold serial dilutions were prepared from the starting concentration for each buffer type. 50 µl of each substrate titration was then added to 50 µl of NanoLuc® luciferase diluted to 4 ng/ml in TBS+0.01% BSA. Samples were incubated for three minutes and then luminescence was measured using a GloMax®-Multi+luminometer.

Substrate Titration:

Furimazine and TAK-0052 were diluted to 100 µM in NanoGlo® buffer or 50 µM in TBS+0.01% BSA. Two fold serial dilutions were prepared from the starting concentration for each buffer type. 50 µl of each substrate titration was then added to 50 µl of NanoLuc® luciferase diluted to 4 ng/ml inTBS+0.01% BSA. Samples were incubated for three minutes and then luminescence was measured using a GloMax®-Multi+luminometer. Results are shown in FIG. 3B.

Figure 3C:
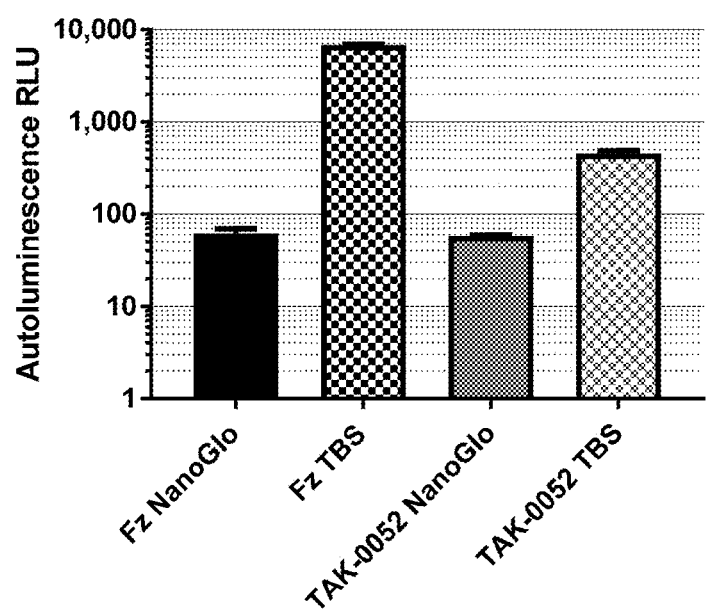
FIG. 3C shows representative results of autoluminescence. Furimazine and TAK-0052 were diluted to 100 µM in NanoGlo® buffer or 50 µM in TBS+0.01% BSA. 50 µl of each substrate buffer combination was added to 50 µl of TBS+0.01% BSA. Samples were incubated for three minutes and then luminescence was measured using a GloMax®-Multi+luminometer.

Autoluminescence:

Furimazine and TAK-0052 were diluted to 100 µM in NanoGlo® buffer or 50 µM in TBS+0.01% BSA. 50 µl of each substrate buffer combination was added to 50 µl of TBS+0.01% BSA. Samples were incubated for three minutes and then luminescence was measured using a GloMax®-Multi+luminometer. Results are shown in FIG. 3C.

Example 6. Luminescent Properties

Figure 4:
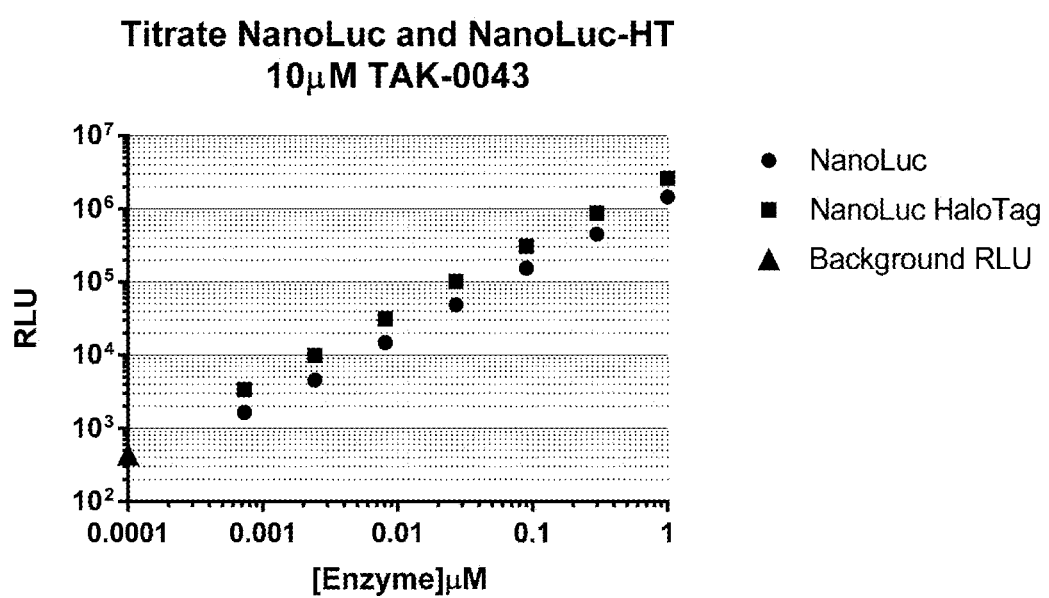
FIG. 4 shows bioluminescent activity of TAK-0043. A dilution series of purified NanoLuc® enzyme (Promega E499a) and purified NanoLuc-Halotag fusion enzyme were prepared in OptiMEM+0.1% FBS starting at a concentration of 2 µM. Three fold serial dilutions (300 µL in 700 µL) of each enzyme were prepared in OptiMEM+0.1% FBS. TAK-0043 was diluted to a concentration of 20 µM in NanoGlo® buffer. 50 µL of each enzyme dilution were combined with 50 µL of TAK-0043 in NanoGlo® buffer. Samples were incubated for three minutes at room temperature and then read on a GloMax® Multi+luminometer.

Luminescence Assay Procedure:

A dilution series of purified NanoLuc® (Promega E499a) and purified NanoLuc-Halotag fusion were prepared in OptiMEM+0.1% FBS starting at a concentration of 2 µM. Three fold serial dilutions (300 µl in 700 µl) of each enzyme were prepared in OptiMEM+0.1% FBS. TAK-0043 was diluted to a concentration of 20 µM in NanoGlo® buffer. 50 µl of each enzyme dilution were combined with 50 µl of TAK-0043 in NanoGlo® buffer. Samples were incubated for three minutes at room temperature and then read on a GloMax® Multi+luminometer. Results are shown in FIG. 4.

Example 7. Cell Permeability and Bioluminescent Activity

Cell Culture:

HeLa and HEK293 cells were maintained in DMEM containing 0.3 mg/ml glutamine, 100 IU/ml penicillin, 100 µg/ml streptomycin, and 10% fetal calf serum at 37° C. in 5% $CO_2$. Dulbecco's modified eagle medium (DMEM), Opti-MEM, Penicillin/Streptomycin, and Trypsin-EDTA are purchased from Life Technologies (Carlsbad). Fetal calf serum (FBS) is purchased from HyClone (GE Healthcare). Microtiter plates were purchased from Corning.

Cell Based Luciferase Assay:

HEK293 cells stably expressing NANOLUC® luciferase under the control of a CMV promotor were plated in 100 µl growth medium (DMEM supplemented with 10% FBS) into wells of white, TC-treated, 96-well plates at a density of 10000 cells per well and incubated for 24 h. The growth medium was then replaced with 100 µl OptiMEM containing 12.5 µM of the indicated substrate. The luminescent signal was analyzed immediately following substrate addition using a GLOMAX® Discover multimode detection plate reader (Promega).

Cell Viability Assay:

HEK293 or HeLa cells were plated in 100 µl growth medium (DMEM supplemented with 10% FBS) into wells of white, TC-treated, 96-well plates at a density of 10,000 cells per well and incubated for 24 h. The growth medium was then replaced with 100 µl Opti-MEM medium that contained a serial dilution of the indicated compound. Changes in cell viability were then measured after incubation for 24 h using the CELLTITER® Green cell viability assay (Promega) according to manufacturer instructions. All luminescent measurements were performed on a GLOMAX® Discover multimode plate reader (Promega).

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

---

What is claimed is:

1. A compound of formula (I)

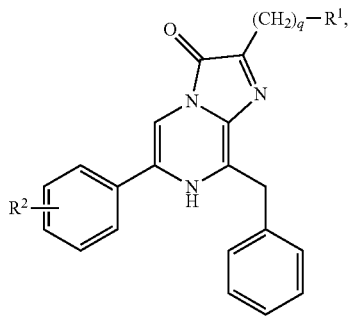

or a tautomer, or a pharmaceutically acceptable salt thereof, wherein
$R^1$ is;

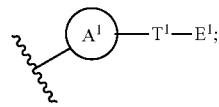

$R^2$ is absent or a substituent selected from the group consisting of alkyl, haloalkyl, halogen, —OH, and —NH$_2$;

$A^1$ is aryl, heteroaryl, heterocyclyl, or cycloalkyl, wherein the aryl, heteroaryl, heterocyclyl, and cycloalkyl are unsubstituted or substituted with 1, 2, 3, 4, 5, 6, 7, 8, 9, or 10 substituents, each independently selected from the group consisting of halogen, oxo, thioxo, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocyclyl, cycloalkylalkyl, heteroarylalkyl, arylalkyl, hydroxy, hydroxyalkyl, alkoxy, alkoxyalkyl, aryloxy, benzyloxy, amino, alkylamino, dialkylamino, acylamino, aminoalkyl, arylamino, sulfonylamino, sulfinylamino, alkylsulfonyl, arylsulfonyl, aminosulfonyl, —COOH, amide, carbamate, silyl, t-butyldimethylsilyl, alkylsulfanyl, and acyl;

$T^1$ is alkyl, alkenyl, alkynyl, or heteroalkyl, wherein the alkyl, alkenyl, alkynyl, and heteroalkyl are unsubstituted or substituted with 1, 2, 3, 4, 5, 6, 7, 8, 9, or 10 substituents, each independently selected from the group consisting of halogen, oxo, thioxo, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocyclyl, cycloalkylalkyl, heteroarylalkyl, arylalkyl, hydroxy, hydroxyalkyl, alkoxy, alkoxyalkyl, aryloxy, benzyloxy, amino, alkylamino, dialkylamino, acylamino, aminoalkyl, arylamino, sulfonylamino, sulfinylamino, alkylsulfonyl, arylsulfonyl, aminosulfonyl, —COOH, ketone, amide, carbamate, silyl, t-butyldimethylsilyl, alkylsulfanyl, and acyl;

$E^1$ is an energy acceptor, wherein the energy acceptor is a fluorescent dye, a quencher, a fluorescent particle, a luminescent metal complex, or a combination of any of the foregoing; and q is 0, 1, or 2.

2. The compound of claim 1, or a tautomer, or a pharmaceutically acceptable salt thereof, wherein $A^1$ is phenyl optionally substituted with 0, 1, 2, 3, or 4 substituents, each independently selected from the group consisting of halogen, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocyclyl, cycloalkylalkyl, heteroarylalkyl, arylalkyl, hydroxy, hydroxyalkyl, alkoxy, alkoxyalkyl, aryloxy, benzyloxy, amino, alkylamino, dialkylamino, acylamino, aminoalkyl, arylamino, sulfonylamino, sulfinylamino, alkylsulfonyl, arylsulfonyl, aminosulfonyl, —COOH, amide, carbamate, silyl, t-butyldimethylsilyl, alkylsulfanyl, and acyl.

3. The compound of claim 1, or a tautomer, or a pharmaceutically acceptable salt thereof, wherein $A^1$ is phenyl optionally substituted with 0, 1, 2, 3, or 4 substituents, wherein each substituent independently is halogen.

4. The compound of claim 1, or a tautomer, or a pharmaceutically acceptable salt thereof, wherein $T^1$ is heteroalkyl.

5. The compound of claim 1, or a tautomer, or a pharmaceutically acceptable salt thereof, wherein $T^1$ is

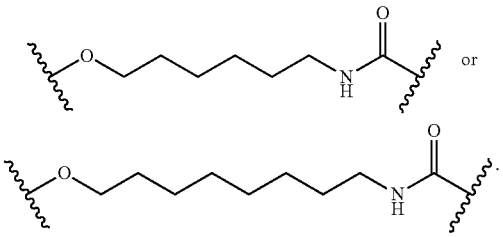

6. The compound of claim 1, or a tautomer, or a pharmaceutically acceptable salt thereof, wherein $T^1$ is —O—$CR^{1a}R^{1b}$—$CR^{1a}R^{1b}$)$_m$-Q- or —O—$(CR^{1a}R^{1b})_n$-Q-, and wherein m is 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30;

n is 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30;

Q at each occurrence is independently —NH—CO—, —CO—NH—, —CO—O—, —O—CO—, or —O—CO—NH—; and $R^{1a}$ and $R^{1b}$ at each occurrence is independently hydrogen or $C_1$-$C_4$ alkyl.

7. The compound of claim 1, or a tautomer, or a pharmaceutically acceptable salt thereof, wherein $R^2$ is absent.

8. The compound of claim 1, or a tautomer, or a pharmaceutically acceptable salt thereof, wherein the energy acceptor is a fluorescent non-chloro TOM dye.

9. The compound of claim 1, or a tautomer, or a pharmaceutically acceptable salt thereof, wherein the energy acceptor has the formula:

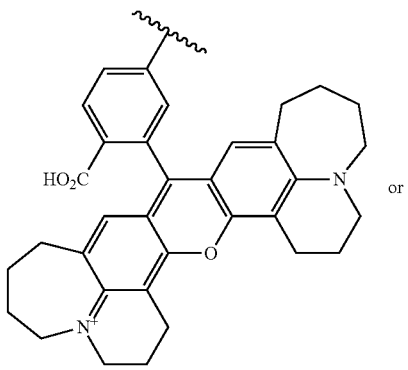

or

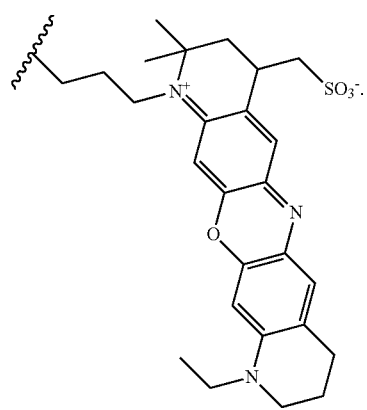

10. The compound of claim 1, wherein the compound has formula (I-a), or a tautomer, or a pharmaceutically acceptable salt thereof:

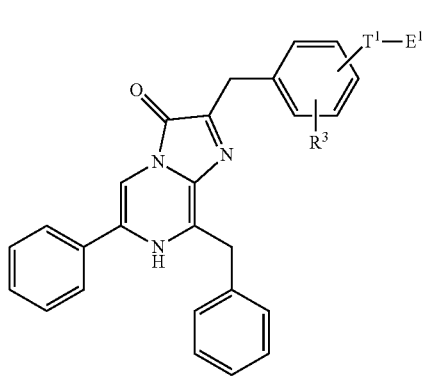

(I-a)

wherein $R^3$ is absent or halogen.

11. The compound of claim 1, wherein the compound has formula (I-b), or a tautomer, or a pharmaceutically acceptable salt thereof:

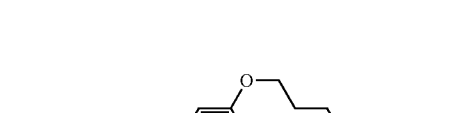

(I-b)

wherein n is 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30.

12. The compound of claim 11, or a tautomer, or a pharmaceutically acceptable salt thereof, wherein n is 6 or 8.

13. The compound of claim 1, wherein the compound has formula (I-c) or formula (I-d), or a tautomer, or a pharmaceutically acceptable salt thereof:

(I-c)

(I-d)

14. The compound of claim 1, which is TAK-0043 or TAK-0052:

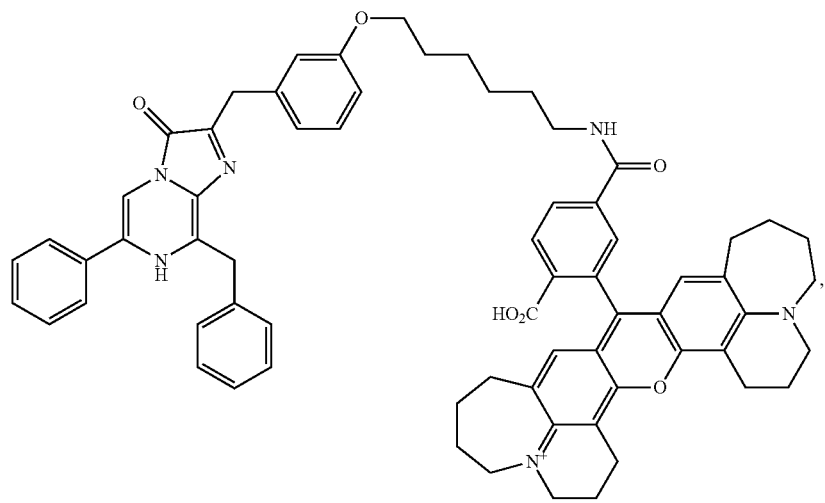

TAK-0043

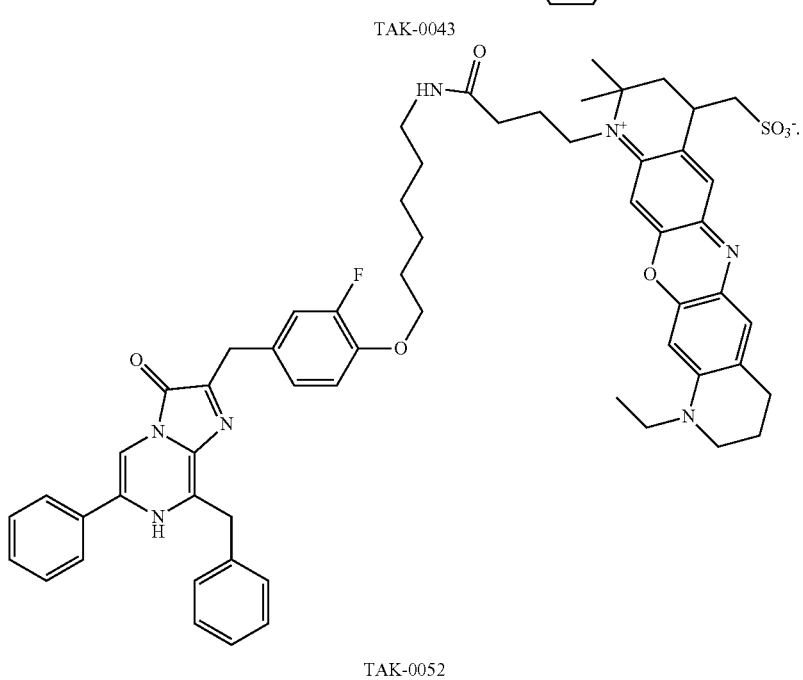

TAK-0052 or a tautomer, or a pharmaceutically acceptable salt thereof.

15. A bioluminescence resonance energy transfer system comprising a compound of claim 1, or a tautomer, or a pharmaceutically acceptable salt thereof.

16. A method of detecting an enzyme in a sample, the method comprising:
   (a) contacting the sample with a compound of claim 1, or a tautomer, or a pharmaceutically acceptable salt thereof; and
   (b) detecting luminescence in the sample.

17. A method for detecting luminescence in a sample, the method comprising:
   (a) contacting a sample with a compound of claim 1, or a tautomer, or a pharmaceutically acceptable salt thereof;
   (b) contacting the sample with a coelenterazine-utilizing luciferase, if it is not present in the sample; and
   (c) detecting luminescence.

18. The method of claim 17, wherein the sample contains live cells.

19. The method of claim 17, wherein the sample contains a coelenterazine-utilizing luciferase.

20. A method for detecting luminescence in a transgenic animal expressing a coelenterazine-utilizing luciferase, the method comprising:
   (a) administering to the transgenic animal a compound of claim 1, or a tautomer, or a pharmaceutically acceptable salt thereof; and
   (b) detecting luminescence.

* * * * *

SEQUENCE LISTING

```
<160> NUMBER OF SEQ ID NOS: 2

<210> SEQ ID NO 1
<211> LENGTH: 169
<212> TYPE: PRT
```

```
<213> ORGANISM: Artificial
<220> FEATURE:
<223> OTHER INFORMATION: Synthetic Peptide

<400> SEQUENCE: 1

Phe Thr Leu Ala Asp Phe Val Gly Asp Trp Gln Gln Thr Ala Gly Tyr
1               5                   10                  15

Asn Gln Asp Gln Val Leu Glu Gln Gly Gly Leu Ser Ser Leu Phe Gln
            20                  25                  30

Ala Leu Gly Val Ser Val Thr Pro Ile Gln Lys Val Val Leu Ser Gly
        35                  40                  45

Glu Asn Gly Leu Lys Ala Asp Ile His Val Ile Ile Pro Tyr Glu Gly
50                  55                  60

Leu Ser Gly Phe Gln Met Gly Leu Ile Glu Met Ile Phe Lys Val Val
65                  70                  75                  80

Tyr Pro Val Asp Asp His His Phe Lys Ile Ile Leu His Tyr Gly Thr
                85                  90                  95

Leu Val Ile Asp Gly Val Thr Pro Asn Met Ile Asp Tyr Phe Gly Arg
            100                 105                 110

Pro Tyr Pro Gly Ile Ala Val Phe Asp Gly Lys Gln Ile Thr Val Thr
        115                 120                 125

Gly Thr Leu Trp Asn Gly Asn Lys Ile Tyr Asp Glu Arg Leu Ile Asn
130                 135                 140

Pro Asp Gly Ser Leu Leu Phe Arg Val Thr Ile Asn Gly Val Thr Gly
145                 150                 155                 160

Trp Arg Leu Cys Glu Asn Ile Leu Ala
                165

<210> SEQ ID NO 2
<211> LENGTH: 171
<212> TYPE: PRT
<213> ORGANISM: Artificial
<220> FEATURE:
<223> OTHER INFORMATION: Synthetic Peptide

<400> SEQUENCE: 2

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
130                 135                 140

Ile Asn Pro Asp Gly Ser Leu Leu Phe Arg Val Thr Ile Asn Gly Val
145                 150                 155                 160
```

```
Thr Gly Trp Arg Leu Cys Glu Arg Ile Leu Ala
            165                 170
```